(12) United States Patent
Rose et al.

(10) Patent No.: US 7,736,591 B2
(45) Date of Patent: Jun. 15, 2010

(54) METHOD AND APPARATUS FOR LIQUID DISPENSING

(75) Inventors: Don Rose, Chapel Hill, NC (US); Thomas C. Tisone, Orange, CA (US)

(73) Assignee: Biodot, Inc., Irvine, CA (US)

( * ) Notice: Subject to any disclaimer, the term of this patent is extended or adjusted under 35 U.S.C. 154(b) by 1257 days.

(21) Appl. No.: 10/421,636

(22) Filed: Apr. 22, 2003

(65) Prior Publication Data

US 2004/0072365 A1 Apr. 15, 2004

Related U.S. Application Data

(60) Division of application No. 09/459,245, filed on Dec. 10, 1999, now Pat. No. 6,551,557, which is a continuation-in-part of application No. 09/348,787, filed on Jul. 7, 1999, now abandoned.

(60) Provisional application No. 60/091,928, filed on Jul. 7, 1998, provisional application No. 60/106,719, filed on Nov. 2, 1998, provisional application No. 60/113,062, filed on Dec. 21, 1998, provisional application No. 60/138,464, filed on Jun. 10, 1999, provisional application No. 60/139,024, filed on Jun. 14, 1999.

(51) Int. Cl.
*B01L 3/02* (2006.01)

(52) U.S. Cl. ............... 422/100; 73/863.32; 73/864; 73/864.01; 73/864.02; 73/864.11

(58) Field of Classification Search ........... 422/99–100; 73/863.32, 864, 864.01, 864.02, 864.11
See application file for complete search history.

(56) References Cited

U.S. PATENT DOCUMENTS 3,164,304 A   1/1965   Jager et al.

(Continued)

FOREIGN PATENT DOCUMENTS

EP    0 082 263 A1    6/1983

(Continued)

OTHER PUBLICATIONS

Shalon, Dari, Stephen J. Smith, and Patrick O. Brown, *A DNA Microarray System for Analyzing Complex DNA Samples Using Two-color Fluorescent Probe Hybridization*, Genome Research, 1996, pp. 839-645.

(Continued)

*Primary Examiner*—Brian R Gordon
(74) *Attorney, Agent, or Firm*—Knobbe Martens Olson & Bear LLP

(57) ABSTRACT

The present invention relates to a ceramic tip and a random access print head for the transfer of microfluidic quantities of fluid. The print head can randomly collect and deposit fluid samples to transfer the samples from a source plate to a target. The print head can also be programmed to create a direct map of the fluid samples from the source plate on the target or to create any desired pattern or print on the target. The tip and print head can be used for a wide variety of applications such as DNA microarraying and compound reformatting. In one preferred embodiment, the tip is used as a capillary or "gravity" pin to draw or collect source fluid and "spot" or deposit the fluid onto the target via physical contact (touch-off). In another preferred embodiment, the tip is used in conjunction with an aspirate-dispense system to actively aspirate source fluid and deposit the fluid via a contact or non-contact approach. The tip provides improved, accurate and repeatable microfluidic transfer.

27 Claims, 13 Drawing Sheets

U.S. PATENT DOCUMENTS

| | | |
|---|---|---|
| 3,568,735 A | 3/1971 | Lancaster |
| 4,058,370 A | 11/1977 | Suovaniemi |
| 4,106,911 A | 8/1978 | Marcelli |
| 4,158,035 A | 6/1979 | Haase et al. |
| 4,199,013 A | 4/1980 | Relch et al. |
| 4,278,205 A | 7/1981 | Binoche |
| 4,318,884 A | 3/1982 | Suzuki |
| 4,323,537 A | 4/1982 | Mody |
| 4,369,664 A | 1/1983 | Bunce et al. |
| 4,418,356 A | 11/1983 | Reece |
| 4,444,062 A | 4/1984 | Bennett et al. |
| 4,461,328 A | 7/1984 | Kenney |
| 4,478,094 A | 10/1984 | Salomaa et al. |
| 4,498,510 A | 2/1985 | Minshew, Jr. et al. |
| 4,516,437 A | 5/1985 | Pedroso et al. |
| 4,530,463 A | 7/1985 | Hiniker et al. |
| 4,699,884 A | 10/1987 | Noss et al. |
| 4,877,745 A | 10/1989 | Hayes et al. |
| 4,922,852 A | 5/1990 | Price |
| 4,926,701 A | 5/1990 | Tompkins |
| 4,944,922 A | 7/1990 | Hayashi |
| 4,971,763 A | 11/1990 | Columbus |
| 5,132,088 A | 7/1992 | Wakatake |
| 5,158,748 A | 10/1992 | Obi et al. |
| 5,260,030 A | 11/1993 | DeVaughn |
| 5,312,757 A | 5/1994 | Matsuyama et al. |
| 5,324,480 A | 6/1994 | Shumate et al. |
| 5,334,353 A | 8/1994 | Blattner |
| 5,338,688 A | 8/1994 | Deeg et al. |
| 5,506,142 A | 4/1996 | Mahaffey et al. |
| 5,508,200 A | 4/1996 | Tiffany et al. |
| 5,529,756 A | 6/1996 | Brennan |
| 5,542,289 A | 8/1996 | Hool et al. |
| 5,558,838 A * | 9/1996 | Uffenheimer ............... 422/100 |
| 5,592,289 A | 1/1997 | Norris |
| 5,593,893 A | 1/1997 | Kobashi et al. |
| 5,599,695 A | 2/1997 | Pease et al. |
| 5,601,980 A | 2/1997 | Gordon et al. |
| 5,601,982 A | 2/1997 | Sargent et al. |
| 5,639,426 A | 6/1997 | Kerr et al. |
| 5,639,665 A | 6/1997 | Arai et al. |
| 5,658,802 A | 8/1997 | Hayes et al. |
| 5,660,792 A | 8/1997 | Koike |
| 5,738,728 A | 4/1998 | Tisone |
| 5,741,554 A | 4/1998 | Tisone |
| 5,742,304 A | 4/1998 | Richtsmeier et al. |
| 5,743,960 A | 4/1998 | Tisone |
| 5,744,305 A | 4/1998 | Fodor et al. |
| 5,747,102 A | 5/1998 | Smith et al. |
| 5,756,050 A | 5/1998 | Ershow et al. |
| 5,763,278 A | 6/1998 | Sickinger et al. |
| 5,770,151 A | 6/1998 | Roach et al. |
| 5,770,160 A | 6/1998 | Smith et al. |
| 5,807,522 A | 9/1998 | Brown et al. |
| 5,807,524 A | 9/1998 | Kelly et al. |
| 5,811,306 A | 9/1998 | Komatsu |
| 5,853,894 A * | 12/1998 | Brown ......................... 428/422 |
| 5,882,930 A | 3/1999 | Baier |
| 5,885,430 A | 3/1999 | Keman et al. |
| 5,916,524 A | 6/1999 | Tisone |
| 5,925,732 A | 7/1999 | Ecker et al. |
| 5,927,547 A | 7/1999 | Papen et al. |
| 5,957,167 A | 9/1999 | Feygin |
| 5,962,329 A | 10/1999 | Ershov et al. |
| 5,976,470 A | 11/1999 | Maiefski et al. |
| 5,985,214 A | 11/1999 | Stylli et al. |
| 6,001,309 A | 12/1999 | Gamble et al. |
| 6,024,925 A | 2/2000 | Little et al. |
| 6,051,190 A | 4/2000 | Birch et al. |
| 6,063,339 A | 5/2000 | Tisone et al. |
| 6,074,609 A | 6/2000 | Gavin et al. |
| 6,101,946 A | 8/2000 | Martinsky |
| 6,110,426 A | 8/2000 | Shalon et al. |
| 6,114,178 A * | 9/2000 | Dezael et al. ............... 436/180 |
| 6,116,297 A | 9/2000 | Feygin |
| 6,203,759 B1 * | 3/2001 | Pelc et al. .................. 422/100 |
| 6,212,949 B1 | 4/2001 | Inder et al. |
| 6,238,626 B1 | 5/2001 | Higuchi et al. |
| 6,255,119 B1 | 7/2001 | Baier |
| 6,485,690 B1 * | 11/2002 | Pfost et al. .................. 422/102 |
| 6,537,505 B1 * | 3/2003 | LaBudde et al. ............ 422/103 |
| 2001/0019845 A1 | 9/2001 | Bienert et al. |
| 2001/0044157 A1 | 11/2001 | Shaion et al. |
| 2001/0048899 A1 | 12/2001 | Marouiss et al. |
| 2002/0001544 A1 | 1/2002 | Hess et al. |
| 2003/0207464 A1 * | 11/2003 | Lemmo et al. .............. 436/180 |
| 2003/0215957 A1 | 11/2003 | Lemmo et al. |

FOREIGN PATENT DOCUMENTS

| | | |
|---|---|---|
| EP | 0 246 632 | 11/1987 |
| FR | 882 339 | 6/1942 |
| GB | 2310006 A | 12/1995 |
| JP | JO 1210039 | 8/1989 |
| WO | WO 87/07377 | 5/1987 |
| WO | WO 96/29595 | 3/1996 |
| WO | WO 00/08474 | 2/2000 |

OTHER PUBLICATIONS

Jacob, Paul. *The Race to Crack the Gene Code*, Los Angeles Times, Thursday Oct. 29, 1998.

Wickelgren, Ingrid. *Gene Readers*, Popular Science, Nov. 1998, pp. 56-61.

*TeleChem International, Inc. Homepage*, TeleChem International, Inc. WebSite, http://arrayit.com/, Aug. 1999.

*ArrayIt™ DNA MIcroarray Product Reference*, TeleChem International, Inc. WebSite, http://arrayit.com/DNA-microarray-products/, Jul. 1999.

*ArrayIt™ Stealth Micro Spotting Technology*, TeleChem International, Inc. WebSite, http://arrayit.com/biochip4/, Jun. 1999.

*PixSys™ PA Series-Microarrayer for Microarray Biochip Fabrication*, TeleChem International, Inc. WebSite, http://arrayit.com/cartesian/, Jan. 1998.

*ArrayIt™ "Bubble" Micro Spotting Pins*, TeleChem International, Inc. WebSite, http://arrayit.com/bubble/, Nov. 1998.

*ArrayIt™ ChipMaker 3*, TeleChem International, Inc., WebSite, http://arrayit.com/biochip3, Mar. 1999.

*ArrayIt™ ChipMaker™ 2*, TeleChem International, Inc. WebSite, http://arrayit.com/biochip/, Mar. 1999.

*Custom ArrayIt™ ChipMaker Printhead for the Hamilton Microlab 2200*—Catalog # CPHH2200, TeleChem International, Inc. WebSite, http://arrayit.com/hamilton/, Jan. 1999.

*ArrayIt™ ChipScript™ Software Version 1.0 (Motion Control Programs for the Cartesian PixSys 5500 Robot Handbook*, TeleChem International, Inc. WebSite, http:/arryit.com/chipscript/, © Copyright 1999.

International Search Report corresponding to PCT/US99/15214.

* cited by examiner

METHOD AND APPARATUS FOR LIQUID DISPENSING

RELATED APPLICATIONS

This application is a divisional of U.S. application Ser. No. 09/459,245, filed Dec. 10, 1999, now U.S. Pat. No. 6,551,557, which is a continuation-in-part of U.S. application Ser. No. 09/348,787, filed Jul. 7, 1999, now abandoned which claims priority to U.S. Provisional Application No. 60/091,928, filed Jul. 7, 1998, U.S. Provisional Application No. 60/106,719, filed Nov. 2, 1998, U.S. Provisional Application No. 60/113,062, filed Dec. 21, 1998, U.S. Provisional Application No. 60/138,464, filed Jun. 10, 1999, and U.S. Provisional Application No. 60/139,024, filed Jun. 14, 1999, the entirety of each one of which is hereby incorporated by reference herein.

PARTIES OF JOINT RESEARCH AGREEMENT

The present invention was the subject of a joint research agreement between BioDot, Inc. and Cartesian Technologies, Inc.

BACKGROUND OF THE INVENTION

1. Field of the Invention

The present invention relates generally to the transfer of microfluidic quantities of fluids and, in particular, to a tip design and random access tip array for genomic applications and high throughput screening.

2. Background of the Related Art

There is an ongoing effort, both public and private, to spell out the entire human genetic code by determining the structure of all 100,000 or so human genes. Also, simultaneously, there is a venture to use this genetic information for a wide variety of genomic applications. These include, for example, the creation of microarrays of DNA material on targets or substrates to create an array of spots on microscope slides or biochip devices. These arrays can be used to read a particular human's genetic blueprint. The arrays decode the genetic differences that make one person chubbier, happier or more likely to get heart disease than another. Such arrays could detect mutations, or changes in an individual's chemical or genetic make-up, that might reveal something about a disease or a treatment strategy.

It can be a difficult task to efficiently and accurately create DNA microarrays. The desired density of the microarrays can be as high as several thousand dots/cm$^2$. Moreover, the desired volume transfer can be low enough to be in the picoliter range.

One typical way of forming DNA microarrays utilizes pins that can be dipped into solutions of the sample fluid(s) and then touched to a surface to create a small spot or dot. The pins are typically thin rods of stainless steel which have a sharpened fine point to provide a small spot size. Undesirably, the sharp point makes the pins fragile and repeated contact with the surface can lead to damaged pins. This can affect the accuracy of the volume transferred, and hence result in unrepeatable and inconsistent performance. Also, these pins generally allow only a single spot to be formed from a single dip.

More recently, pins have been made with a small slot to permit multiple spotting from a single dip of the sample fluid. Undesirably, the slot can render the pins even more fragile. Another disadvantage of the slotted pin technology is that there is a large variation in the spot size and volume transfer between the first transfer and subsequent transfers—this variation can be as much as 50%. Also, the fluid sample in the slot is undesirably exposed to the atmosphere during the transfer step. This can lead to contamination and evaporation of valuable fluid. Moreover, the pins can have limited reproducibility due to surface tension changes within the slot as solution is dispensed and as solution evaporates from the exposed pin. Additionally, thorough cleaning of the slotted pins can be difficult and time-consuming.

In many cases, the spotting pins are held in a pin holder which allows multiple pins to be dipped into the sample solution and spotted onto the target, typically a glass slide. The spacing between the pins typically corresponds to the spacing between the wells of the source plate. To create high density microarrays, the pins are simultaneously dipped and then spotted. Subsequent spotting is accomplished by offsetting the spotting position by a small distance. One of the disadvantages of this spotting technique is that the location of the samples (spots) on the slide does not correspond to the location of the samples (wells) in the source plate. Another disadvantage is that samples cannot be randomly accessed from the source plate and randomly printed on the slide. These disadvantages diminish the versatility and utility of such conventional microarraying technology.

Conventional pin transfer technology is also used in other applications such as high throughput screening (HTS). High throughput screening involves compound or reagent reformatting from a source plate to an assay plate. For example, test compounds, dissolved in DMSO are transferred from a 96 well plate to a 96, 384 or 1536 well microtiter plate. Typically, the desired transfer volume is higher than that for genomic arraying and is in the range from about 1 to 200 nanoliters (nL) or more. Undesirably, conventional pin transfer technology when utilized for compound reformatting can also suffer from some or all of the above disadvantages.

Microfluidic transfer of liquids can also be performed using an aspirate-dispense methodology. State-of-the-art aspirate-dispense methods and technologies are well documented in the art, for example, as disclosed in U.S. Pat. No. 5,741,554, incorporated herein by reference. These typically use pick-and-place ("suck-and-spit") fluid handling systems, whereby a quantity of fluid is aspirated from a source and dispensed onto a target for testing or further processing. But to efficiently and accurately perform aspirate and dispense operations when dealing with microfluidic quantities, less than 1 microliter (μL), of fluid can be a very difficult task. The complexity of this task is further exacerbated when frequent transitions between aspirate and dispense functions are required. Many applications, such as DNA microarraying and HTS, can involve a large number of such transitions. In these and other applications it is desirable, and sometimes crucial, that the aspirate-dispense system operate efficiently, accurately and with minimal wastage of valuable reagents.

Therefore, there is a need for an improved technology and methodology that provides efficient, repeatable and accurate transfer of microfluidic quantities of fluid while reducing wastage of such fluids.

SUMMARY OF THE INVENTION

The present invention overcomes some or all of the above disadvantages by providing a ceramic tip and a random access print head for the transfer of microfluidic quantities of fluid. Advantageously, the print head can randomly collect and deposit fluid samples to transfer the samples from a source plate to a target. The print head can also be programmed to create a direct map of the fluid samples from the source plate on the target or to create any desired pattern or print on the target. The tip and print head can be used for a wide variety of applications such as DNA microarraying and compound reformatting. In one preferred embodiment, the tip is used as a capillary or "gravity" pin to draw or collect source fluid and "spot," deposit or contact dispense the fluid onto the target via physical contact (touch-off). In another preferred embodiment, the tip is used in conjunction with an aspirate-dispense system to actively aspirate source fluid and deposit the fluid via a contact or non-contact approach. Advantageously, the tip provides improved, accurate and repeatable microfluidic transfer.

In accordance with one preferred embodiment the present invention provides a contact transfer tip for micro-fluidic dispensing of fluid from a fluid source onto a desired target substrate. The contact transfer tip generally comprises a substantially cylindrical upper body portion, a substantially tapered lower body portion and a lumen cavity. The substantially cylindrical upper body portion has a first outside diameter. The substantially tapered lower body portion has a second outside diameter at a transition portion thereof which is substantially equal to the first outside diameter of the upper portion. The substantially tapered lower body portion further has a third diameter at a lower-most end thereof which is smaller than the first or second diameters and which approximately equals the diameter of a spot or dot of fluid desired to be deposited onto the target substrate. The upper and lower body portions are coaxially aligned relative to one another about a central axis. The lower-most end of the lower body portion is substantially flat and lies in a plane substantially normal to the central axis. The lumen cavity is formed so that it extends substantially completely through the upper and lower body portions and forms an orifice or opening at the lower-most end of the lower body portion. The orifice is adapted to admit a quantity of the fluid into the lumen cavity by capillary action when dipped into the fluid source and further adapted to dispense a spot or dot of said fluid when said lower-most end is contacted with said target substrate.

In accordance with another preferred embodiment the present invention provides a random access micro-fluidic contact-transfer dispensing system for selectively dispensing fluid from a fluid source onto a desired target substrate. The dispensing system generally comprises a plurality of contact transfer tips arranged in a generally uniform array. Each of the contact transfer tips has a lumen extending generally therethrough and has an orifice at a lower-most end thereof. The orifice is adapted to admit a quantity of fluid into the lumen cavity by capillary action when the transfer tip is dipped into the fluid source. The orifice is further adapted to dispense a spot or dot of the fluid when the lower-most end is contacted with the target substrate. Each of the contact transfer tips is slidingly fitted within a substantially low-friction alignment sleeve so as to provide a floating effect to each transfer tip. Each of the contact transfer tips is further associated with an actuator responsive to an actuation signal for selectively raising or lowering each contact transfer tip relative to the target substrate and/or fluid source.

In accordance with a further preferred embodiment the present invention provides an apparatus for aspirating and dispensing predetermined microfluidic quantities of a fluid. The apparatus generally comprises a ceramic tip, a drop-on-demand valve and a positive displacement pump. The ceramic tip includes a nozzle with an inner taper to provide improved and generally laminar flow. The drop-on-demand valve is adapted to be opened and closed at a predetermined frequency and/or duty cycle to permit intermittent hydraulic coupling with the tip. The positive displacement pump is hydraulically coupled with the valve for metering predetermined quantities of fluid to or from the tip.

For purposes of summarizing the invention and the advantages achieved over the prior art, certain objects and advantages of the invention have been described herein above. Of course, it is to be understood that not necessarily all such objects and advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENTS

Figure 1:
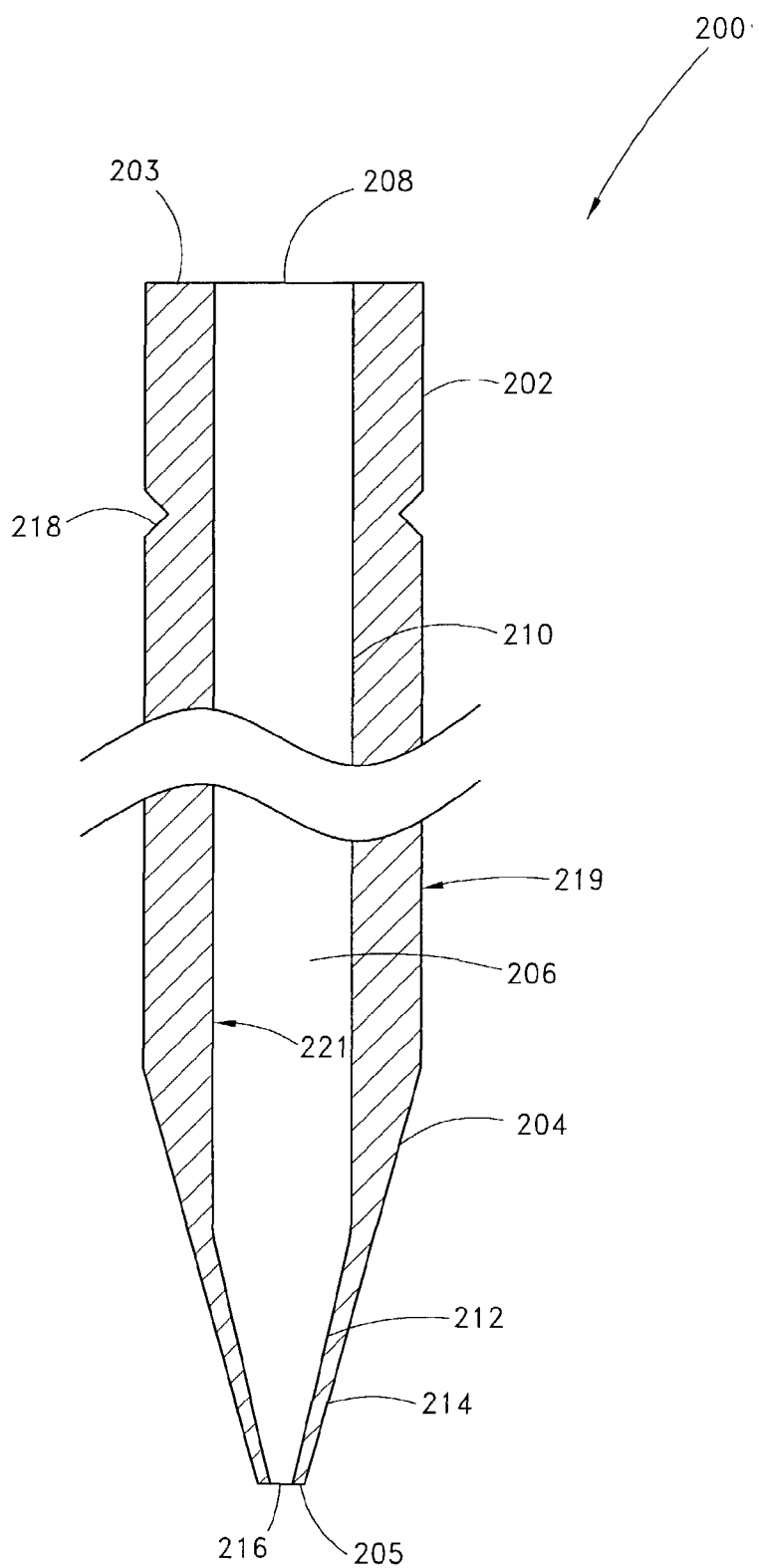
FIG. 1 is a schematic cross section view of a microfluidic transfer tip having features in accordance with one preferred embodiment of the present invention.

FIG. 1 is a schematic cross-section view of a capillary tip, tube or pin 200 having features in accordance with one preferred embodiment of the present invention. As discussed later herein, the tip 200 provides for improved microfluidic transfer of liquids for applications such as genomic microarraying and high throughput screening (HTS). In one preferred embodiment, the tip 200 is used as a capillary or "gravity" pin to draw or collect source fluid and "spot," deposit or contact dispense the fluid onto the target via physical contact (touch-off). In another preferred embodiment, the tip 200 is used in conjunction with an aspirate-dispense system to actively aspirate source fluid and deposit the fluid via a contact or non-contact approach.

In one preferred embodiment, the tip 200 is generally cylindrical in shape and comprises a non-tapered upper portion or shank 202 with an upper end 203, a tapered lower portion/outer surface 204 with a lower end 205 and an inner lumen or through cavity 206. The inner lumen 206 is generally cylindrical in shape with a top opening 208, a non-tapered upper portion 210, and a tapered lower portion/inner surface 212 to form a nozzle 214 having an orifice or opening 216. The lower end 205 of the outer taper 204 generally determines the spot or dot size. Advantageously, the outer taper 204 leads to less accumulation of fluid on the tip outer surface. Also, advantageously, the inner taper 212 is a desirable shape for capillary action, and reduces fluid mixing during aspiration and reduces the precipitation of gaseous bubbles within the fluid during aspirate-dispense operations.

In one preferred embodiment, the tip 200 further includes a generally circumferential groove, slot or notch 218 on the non-tapered upper portion 202. Preferably, the slot 218 is generally V-shaped. The notch 218 advantageously provides an easy break point in the case of accidental hard or jarring contact between the tip 200 and a contacting surface of the fluid target or source.

Preferably, the tip 200 is fabricated from a ceramic material, and more preferably, from alumina. Advantageously, the ceramic material provides chemical inertness since alumina is inert to most chemical solvents. Moreover, the ceramic material provides robustness, and hence can withstand extreme mechanical stress. In other embodiments, the tip 200 can be fabricated from a wide variety of materials with efficacy such as metals, alloys, and plastics, as required or desired, giving due consideration to the goals of providing chemical inertness and robustness.

Figure 2:
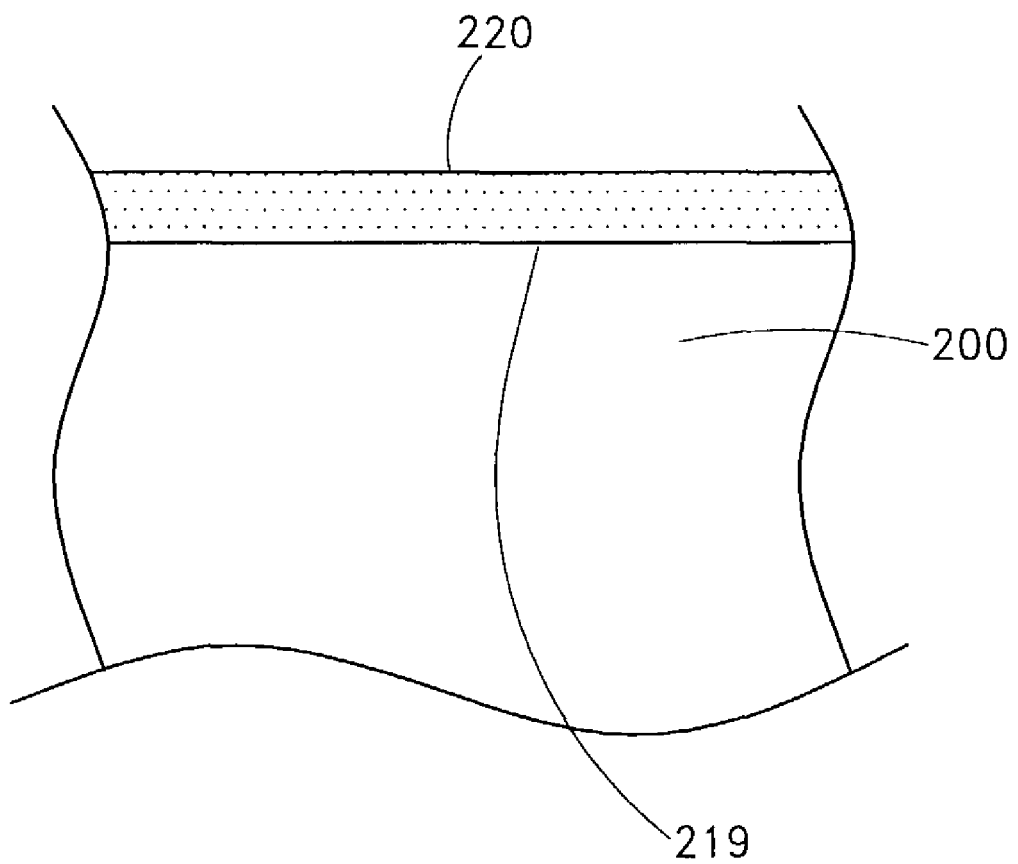
FIG. 2 is a schematic illustration of a hydrophobic coating on the tip of FIG. 1.

In one preferred embodiment, and as schematically illustrated in FIG. 2, the outer surface 219 of the tip 200 is coated with a thin film or coating 220 that is not only chemically inert and mechanically robust but is also hydrophobic to most fluids such as aqueous reagents, DMSO, and other common solvents. The film 220 helps in keeping the tip 200 dry and also improves the microfluidic transfer. Preferably, the film 220 comprises a wear-resistant material so that it has an enhanced lifetime. Suitable coatings 220 are silicon nitride, silicon carbide, titanium nitride, among others. The coating 220 can be applied by a variety of methods such as plasma deposition and sputtering, among others, as is known in the art. A suitable hydrophobic coating may also be applied to the inner surface 221 of the tip 200.

The tip 200 may be dimensioned in a wide variety of manners with efficacy, as required or desired, giving due consideration to the goals of providing reliable and repeatable microfluidic transfer of fluid. In one embodiment, the tip 200 has a length of 16 mm and an internal volume of about 20 microliters (μL). For genomic applications, preferably, the inner diameter at the nozzle end of the tip 200 is in the range from about 20 to 180 microns (μm) and the outer diameter is in the range from about 50 to 400 μm or more. For compound reformatting, preferably, the inner diameter at the nozzle end of the tip 200 is in the range from about 100 to 300 μm and the outer diameter is in the range from about 400 to 900 μm.

Random Access Capillary Pin Array

In one preferred embodiment, and as indicated above, the tip 200 (FIG. 1) is used as a capillary tip or gravity pin. The nozzle 214 of the tip 200 is dipped in a source of fluid or reagent with the top opening 208 vented to atmospheric pressure. Capillary action causes a small volume of fluid to enter the inner lumen 206 through the nozzle orifice 216. The nozzle end 205 is touched to a target surface to transfer the reagent. Advantageously, multiple touch-offs can also be performed at the same or different site to transfer the desired quantity/volume of reagent to the desired target(s) or location(s). As discussed later, a robot arm and/or movable X, X-Y or X-Y-Z platforms can be utilized to provide relative motion between the tip 200, and the target and source.

For genomic applications, the target is typically a glass slide, substrate or membrane, among others. The touch-off or contact transfer leaves a spot, dot or imprint of the fluid on the target. The spot typically has a size approximately the same as the outer diameter of the nozzle end 205. For compound reformatting, the reagent is typically transferred to a microwell of a microtiter plate. In this manner, microfluidic quantities of reagents can be accurately and reliably collected and deposited with good reproducibility utilizing the capillary tip 200 as a microfluidic collection and deposition means. It is believed that the inner taper 212 at the tip nozzle 214 results in reduced local pressure drops during collection and deposition of fluid. Advantageously, this prevents precipitation of unwanted gaseous bubbles from any gas that may be dissolved in the fluid.

Advantageously, during the reagent transfer very little of the reagent in the tip 200 is exposed to the atmosphere. This desirably reduces the evaporation of reagent, and hence reduces wastage of valuable reagent. Moreover, the risk of possible contamination of the reagent is also reduced.

The tip through cavity 206, advantageously, permits rapid and thorough cleaning of the tip 200 by allowing fluid to be forced through the lumen 206, for example, by using a positive displacement pump. Also, desirably, any remaining source fluid within the tip 200 can be transferred back to the source by using a positive displacement pump in communication with the tip 200. This reduces wastage of valuable source fluid.

Figure 3:
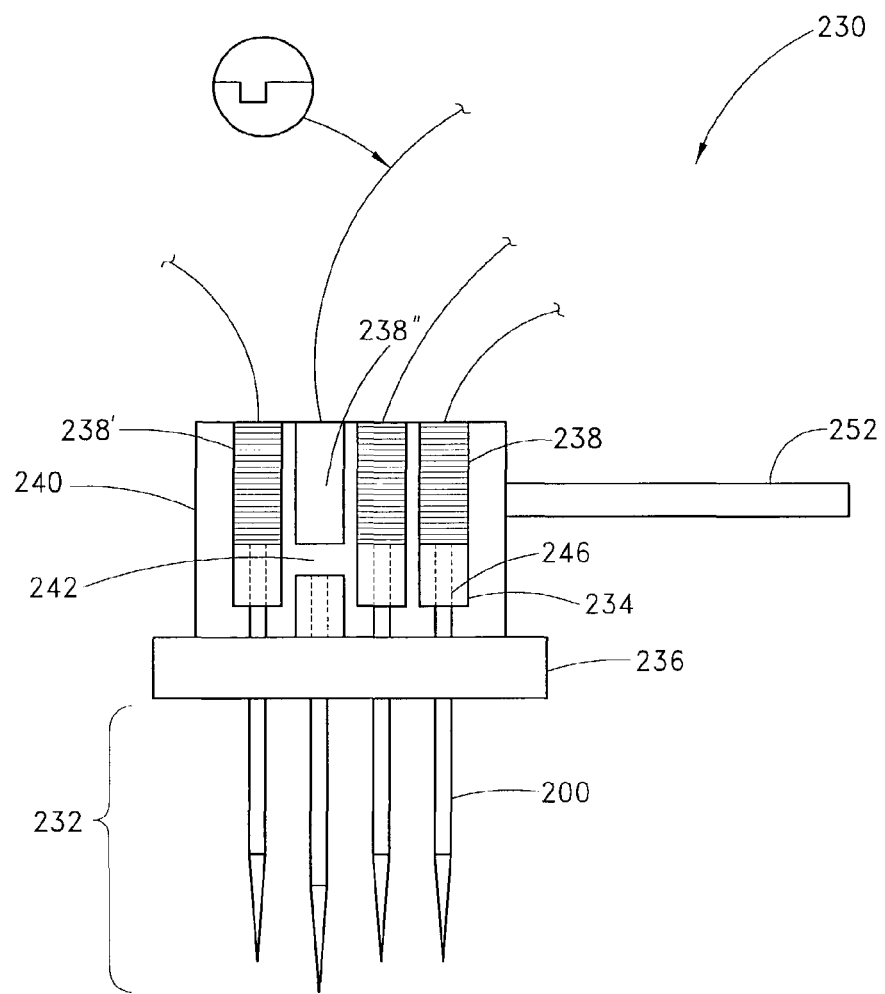
FIG. 3 is a schematic illustration of a random access tip array having features in accordance with one preferred embodiment of the present invention.
Figure 3:
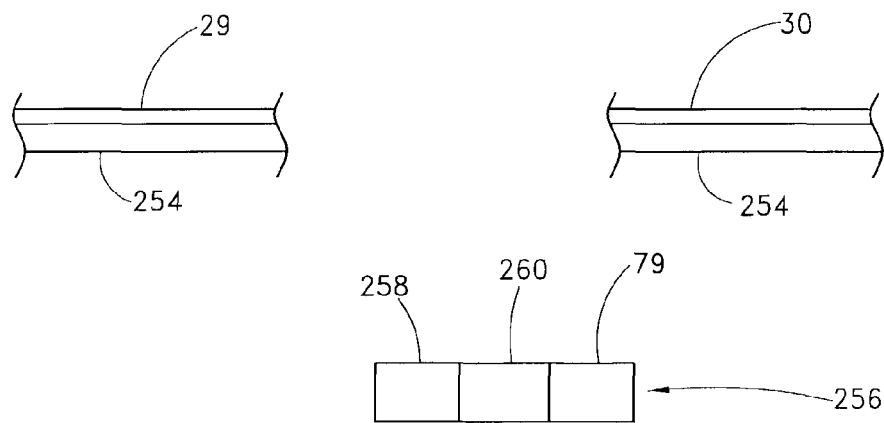

FIG. 3 is a schematic representation of a random access tip/pin array or print head 230 for transferring microfluidic quantities of fluid or reagent. The print head (or random access micro-fluidic contact-transfer dispensing system) 230 generally comprises an array 232 of floating contact transfer tips 200 (FIG. 1) having respective base members 234 mounted on a tip holder, mount or sleeve 236 and a plurality of solenoid actuators 238. The solenoids 238 are mounted in a housing 240 and are positioned above respective tips 200. The tip base 234 is preferably fabricated from a magnetic material, such as a 400 series stainless steel, among other materials. Thus when the solenoids 238 are energized they attract respective bases 234 to close the respective gaps 242 between the respective tips 200 and the respective solenoids 238. In this manner, one or more selected tips 200 may be used for collection and deposition of microfluidic quantities of reagent from a source 29 to a target 30, as required or desired. Advantageously, the print head 230 can be selectively operated to randomly access and deposit from the source 29 to the target 30 and can form a printed array that is a direct map of the reagent locations in the source plate 29, for example, a microtiter plate with a plurality of microwells.

The random access print head 230 can also utilize a wide variety of other pins, tips, and the like for microfluidic transfer. For example, the print head 230 can utilize conventional pins that are thin rods of stainless steel with a sharpened fine point to provide a small spot size. The print head 230 can also utilize conventional slotted pins. Other suitable pins, tips and the like can be used with efficacy, as required or desired, giving due consideration to the goal of providing random collection and/or deposition of microfluidic quantities of fluids.

The floating tip mount 236 (FIGS. 3 and 4) is an air bearing mount with a plurality of holes 244. The holes 244 are machined to a close tolerance to slidingly accommodate the tips 200 while maintaining the alignment of the tips 200. Preferably, the mount 236 is fabricated from brass with a low friction finish. In other embodiments, the mount 236 can be fabricated from a wide variety of materials such as other metals, alloys, ceramics, plastics with efficacy, as required or desired, giving due consideration to the goals of floatingly accommodating the tips 200 and maintaining a high tolerance alignment of the tips 200.

Figure 4:
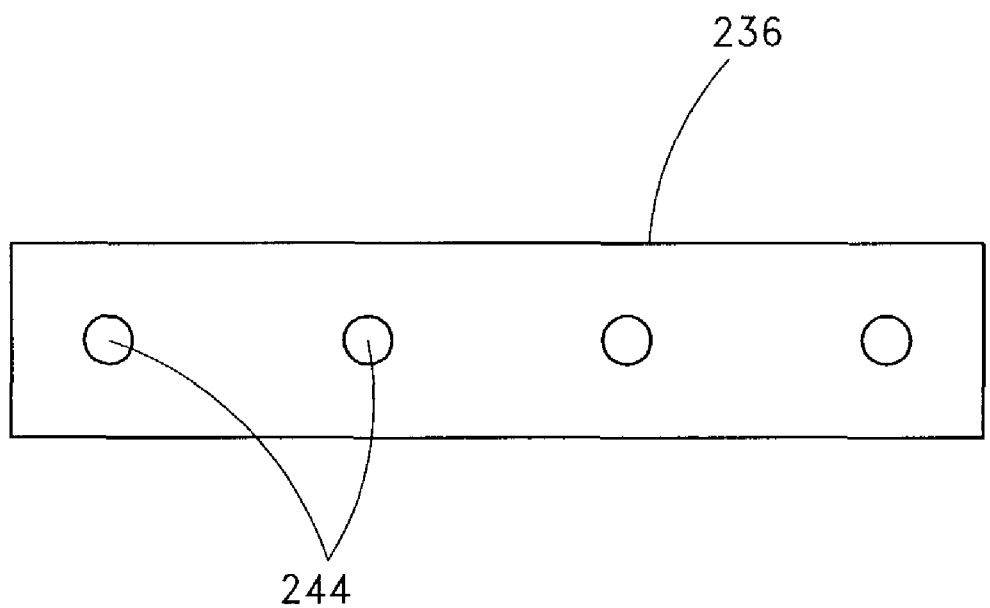
FIG. 4 is a top plan view of an air bearing mount for floatingly holding the tips of FIG. 3.

The tip base member 234 (FIG. 3) has a hole 246 so that the top end 203 (FIG. 1) of the tip 200 can reside in the hole 246 with the top opening 208 (FIG. 1) vented to the atmosphere. The base members 234 can be removably attached to the respective tips 200 so that selected tips 200 can be replaced, if required or desired. This allows differently configured and/or dimensioned tips 200 to be used with the print head 230, and hence adds to the versatility of the invention. The bases 234 also prevent the respective tips 200 to fall through the air bearing mount holes 244 (FIG. 4).

The solenoids 238 (FIG. 3) can be a wide variety of commercially available solenoids and are controlled independently of one another. When the solenoids 238 are energized, for example, the solenoid labeled 238' in FIG. 3, the respective tips 200 are raised as the respective bases 234 are attracted to the respective energized solenoids 238. When the solenoids 238 are not energized, for example, the solenoid labeled 238" in FIG. 3, the respective tips 200 are lowered and the respective base members 234 are seated on the mount 236. In the lowered position the tip(s) 200 can then be used for microfluidic transfer of reagent.

Figure 5:
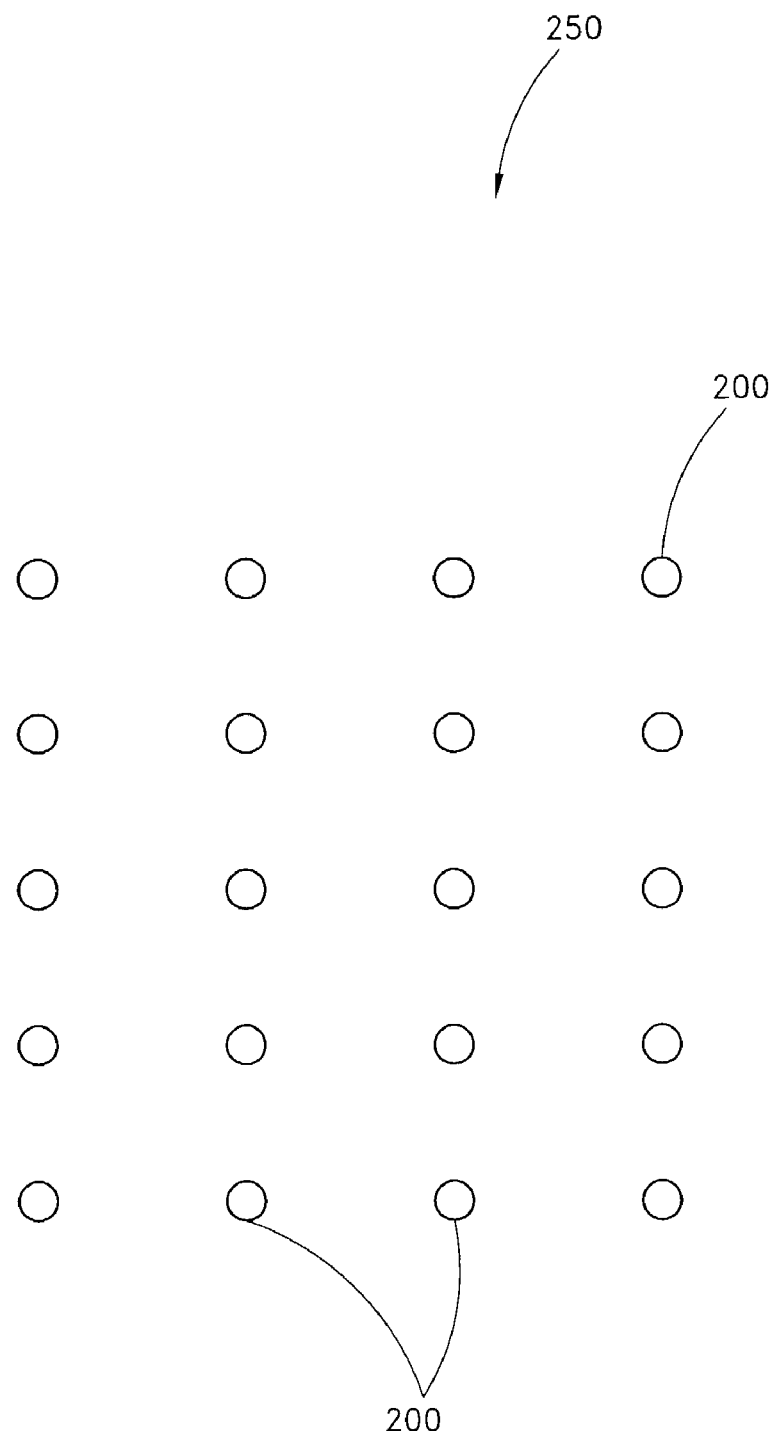
FIG. 5 is a schematic illustration of a two-dimensional tip array.

The spacing between the tips 200 (FIG. 3) generally corresponds to the spacing between the wells of the source plate 29 which is typically about 2.5 mm, 4.5 mm or 9 mm. In other embodiments, the tips 200 can be spaced alternatively depending on the particular use. In one preferred embodiment, the tips 200 are arranged in a line or one-dimensional array 232 as schematically shown in FIG. 3. In another preferred embodiment, schematically illustrated in FIG. 5, the tips 200 are arranged in a two-dimensional array 250. Alternatively, the tips 200 can be arranged in a wide variety of manners as dictated by the particular application. Also, the number of tips 200 used in the array can vary from 1 to 384 or greater. Rectangular arrays comprising $[(4\times2^x)\times(6\times2^x)]$ tips 200 are also convenient to provide 96, 384, 1536, and so on, number of tips 200. Square arrays of $2^x$ can also be used, such as 2, 4, 8, 16, 32, and so on.

Referring to FIG. 3, the random access pin array 230 is moved via a robot arm 252. Also, X, X-Y or X-Y-Z platforms 254 can be utilized to move the source 29 and target 30. A suitable controller can be employed to monitor and control the operation of the various components of the print head 230, such as the solenoids 238, the robot arm 252 and the platforms 254.

In one preferred embodiment, a wash station 256 (FIG. 3) is provided in combination or conjunction with the random access tip array 230 to maintain a dry tip. The wash station 256 generally comprises a vacuum dry system 79 (FIGS. 3 and 6A) to remove any excess fluid that may have adhered to the outer surface of the tip 200 during dipping of the tips 200 in the source reagent or due to any moisture build-up on the outer surface of the tip 200, for example, due to condensation from the air environment. The system 79 (FIG. 6A) generally includes a pump 80 connected to one or more vacuum cavities, apertures or orifices 82. The tips 200 are inserted into the vacuum apertures 82. The pump 80 is activated for a predetermined amount of time and provides enough suction to remove or suck any excess fluid sticking to the outer surface of the tip 200. The pump suction can also be adjusted so that it can remove excess fluid without disturbing any reagent, if present, inside the tip 200. The vacuum dry can also be performed after washing the tips 200 in a cleaning fluid, for example, distilled water, among others. Alternatively, the tips 200 can be dipped in a volatile solvent such as isopropyl alcohol, among others, to maintain a dry tip. Also, as indicated above, the hydrophobic coating 220 (FIG. 2) and the outer taper 204 (FIG. 1) to a small nozzle end 205 (FIG. 1) further assist in keeping the tips 200 dry and free of excess liquid. Optionally, the tips 200 may also be dried by blotting them on an absorbent material.

Figure 6A:
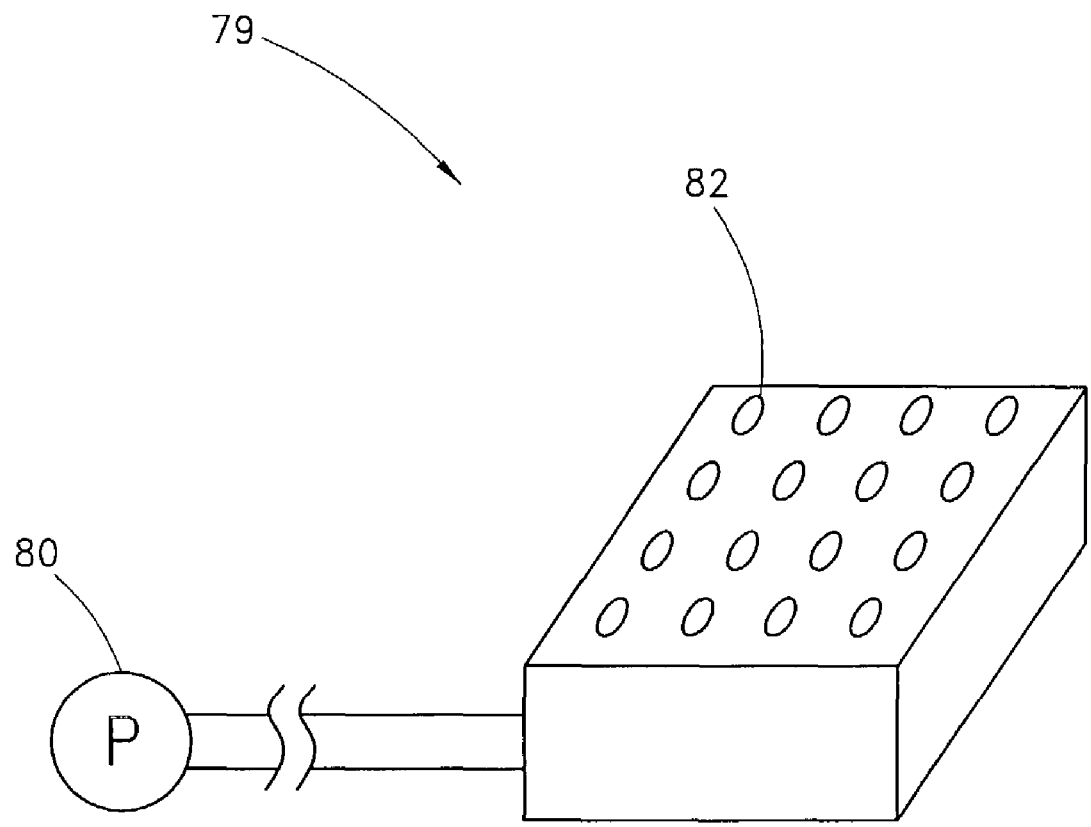
FIG. 6A is a schematic illustration of a vacuum dry system for removing excess fluid from the tips of FIG. 3.

In one preferred embodiment, the wash station 256 (FIG. 3) generally comprises a wash/cleaning bath 258, an ultrasonic bath 260 and the vacuum system 79 (FIG. 6A) for cleaning the tips 200. The tips 200 are dipped in the wash bath 258 and draw wash/cleaning fluid by capillary action. This dilutes any remaining reagent in the tips 200. The tips 200 are then inserted in the vacuum cavities 82 (FIG. 6A) of the vacuum system 79 and the pump 80 is operated to provide enough suction to remove some or all of the fluid from the tips 200. The tips 200 can also be spotted in a waste or other suitable position to remove some or all of the fluid within the tips 200. Also, the vacuum system 79 and the spotting process can be used in combination to remove the fluid from the tips 200. The wash bath cleaning followed by the fluid removal from the tips can be repeated a number of times, as required or desired. Typically two or three cleanses in the wash bath 258 are sufficient. The tips 200 are then further cleaned by dipping in the ultrasonic bath 260. This is followed by a vacuum dry of the tips 200 using the vacuum dry system 79 (FIG. 6A). Optionally, the tips 200 may also be cleaned by blotting them on an absorbent material.

Figure 6B:
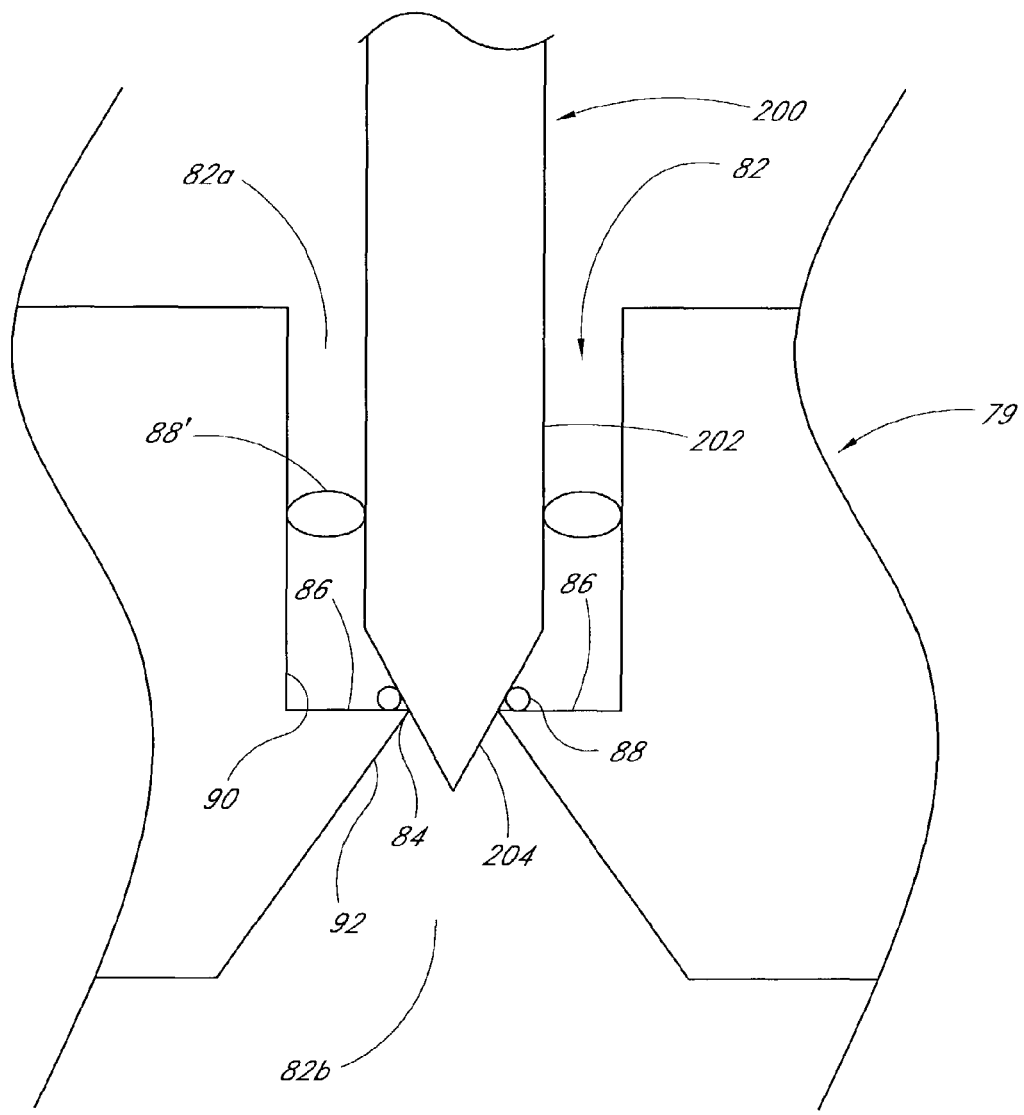
FIG. 6B is a schematic illustration of a vacuum cavity of the system of FIG. 6A having features in accordance with certain preferred embodiments of the present invention.

In one preferred embodiment, and as shown in FIG. 6B, the vacuum cavities or holes 82 of the vacuum dry system 79 comprise an upper cavity or hole 82a and a lower cavity or hole 82b. The upper cavity 82a and the lower cavity 82b are in fluid communication with one another through an opening 84 and are separated by a step or shoulder 86. The upper cavity 82a is sized and configured to accommodate the girth of the non-tapered upper portion or shank 202 of the tip 200. The opening 84 and step 86 are sized and configured to engage the tapered lower portion 204 of the tip 200. Preferably, the step 86 forms a seal or a partial seal with the tip tapered portion 204 when the tip tapered portion 204 engages, contacts or abuts the step 86. Advantageously, this facilitates in the clearing or removal of fluid from inside the tip 200. The step 86 can be substantially rigid in nature or it can comprise a resilient or flexible material, as required or desired, giving due consideration to the goals of forming a seal or partial seal and/or facilitating the cleaning of the tip 200.

In another preferred embodiment, an O-ring or washer 88 (FIG. 6B) is utilized to from a seal or partial seal with the tip tapered portion 204. The O-ring 88 can be substantially rigid in nature or it can comprise a resilient or flexible material, as required or desired, giving due consideration to the goals of forming a seal or partial seal and/or facilitating the cleaning of the tip 200.

The O-ring 88 can be provided on a suitable surface or wall of the vacuum cavity 82, as required or desired, giving due consideration to the goals of providing a seal or partial seal and/or facilitating the cleaning of the tip 200. For example, the O-ring 88 can be seated on the step 86, mounted on a side wall 90 or 92 of the cavity 82 and/or can replace the step 86.

In one preferred embodiment, an O-ring or washer 88' (FIG. 6B) is utilized to from a seal or partial seal with the tip non-tapered portion or shank 202. The O-ring 88' can be substantially rigid in nature or it can comprise a resilient or flexible material, as required or desired, giving due consideration to the goals of forming a seal or partial seal and/or facilitating the cleaning of the tip 200.

The O-ring 88' can be provided on a suitable surface or wall of the vacuum cavity 82, for example, the side wall 90, as required or desired, giving due consideration to the goal of providing a seal or partial seal and/or facilitating the cleaning of the tip 200. The O-ring 88' can be used independently of or in combination with one or both of the step 86 and O-ring 88, as required or desired, giving due consideration to the goal of providing a seal or partial seal and/or facilitating the cleaning of the tip 200.

Referring to FIG. 6B, when the tip 200 is inserted into the vacuum cavity 82 and while the tip 200 is not engaged with the step 86, O-ring 88, or O-ring 88', the vacuum dry system 79 facilitates in the removal or cleaning of fluid from the outer surface of the tip 200. When the tip 200 is sealingly or partially sealingly engaged with the step 86, O-ring 88, or O-ring 88', the vacuum dry system 79 facilitates in the removal or clearing of fluid from inside the tip 200. Advantageously, this allows for improved cleaning of the tip 200, and hence enhanced performance.

In use, initially all the tips 200 (FIG. 3) are raised by energizing the solenoids 238. The print head 230 is positioned and aligned over the source 29 by utilizing the robot arm 252 and/or the movable platforms 254. For random access collection, a first tip 200 is lowered by de-energizing or turning off the corresponding solenoid 238. The first tip 200 dips into a microwell of the source plate 29 to draw fluid by capillary action. The first tip 200 is raised by energizing the corresponding solenoid 238. Relative motion is provided between the source plate 29 and the print head 230, by the robot arm 252 and/or the movable platform 254, to align a second tip 200 with a corresponding microwell of the source plate 29. The second tip 200 is lowered and collects source fluid from the microwell. The second tip 200 is then raised. Subsequent tips 200 are lowered and raised in a similar manner. This random access collection process is continued until all the tips 200 are loaded with the sample fluid.

The print head 230 is then positioned and aligned over the target 30 by the robot arm 252 and/or the movable platforms 254. For random access deposition, a first tip 200 is lowered by de-energizing or turning off the corresponding solenoid 238 and contacts the target 30 to transfer source fluid. The first tip 200 is raised by energizing the corresponding solenoid 238. Relative motion is provided between the target 30 and the print head 230, by the robot arm 252 and/or the movable platform 254, to align a second tip 200 over the target 30. The second tip 200 is lowered and contacts the target 30 to deposit fluid. The second tip 200 is then raised. Subsequent tips 200 are lowered and raised in a similar manner. This random access deposition process is continued until all the tips 200 have deposited the fluid samples from the source plate 29 onto the target 30.

The random access print head 230 (FIG. 3) can be operated in several modes. These modes include a combination of both random access collection and deposition, random access collection only, and random access deposition only. The random access collection and deposition mode utilizes the random access collection process followed by the random access deposition process, as described above.

In the random access collection only mode, source fluids are collected, as described above for the random access collection process. The source fluids are then deposited by simultaneously lowering all the tips 200 over the target 30. Alternatively, more than one but less than all of the tips 200 may be lowered or raised to simultaneously collect or deposit fluid.

In the random access deposition only mode, all the tips 200 are dipped simultaneously into the source plate 29 to collect source fluids. The source fluids are then deposited, as described above for the random access deposition process. Alternatively, more than one but less than all of the tips 200 may be lowered or raised to simultaneously collect or deposit fluid.

Advantageously, the tip 200 can hold a sufficient volume of fluid that allows multiple touch-offs at the same position on the target 30. Moreover, the same reagent may be deposited on different targets 30 after a single dip of the tip 200. This further adds to the versatility of the random access print head 230.

As indicated above, for DNA microarraying the target 30 is generally a glass slide, substrate or membrane, among others, and the tips 200 form dots or spots of the source fluids on the target 30. For DNA microarraying the tips 200 can form dots having a diameter in the range from about 50 µm to greater than about 400 µm and can form arrays having densities in the range from less than about 10 dots/cm$^2$ to greater than about 6000 dots/cm$^2$. The size of these spots or dots is generally determined by the outer diameter of the nozzle end 205 of the tip 200. The tips 200 can also transfer fluid volumes as low as in the picoliter range and up to about 100 nanoliter (nL) or more.

For high throughput screening (compound reformatting) the target 30 is typically a microtiter plate, such as a 96, 384 or 1536 well plate. In this case, the tips 200 can transfer fluid volumes in the range from about 1 nL to about 200 nL or more.

Advantageously, the print head 230 of the present invention can randomly collect and randomly deposit microfluidic quantities of fluid. The print head 230 can also be programmed to create a direct map of the source fluids from the source 29 on the target 30 or to create any desired pattern or print on the target 30. This further adds to the versatility of the present invention. Moreover, the floating tips 200 (FIG. 3) can compensate for any small deviations in flatness on the surface of the source 29 or target 30, since the tips are movably held in the print head 230. This can reduce damage to the tips 200 and other components of the print head 230 in case of possible misalignment with the source 29 and/or target 30. Optionally, one or more optical sensors may be used to monitor the alignment and positioning of the tips 200 relative to the source 29 and target 30.

Aspirate-Dispense Operation

Figure 7:
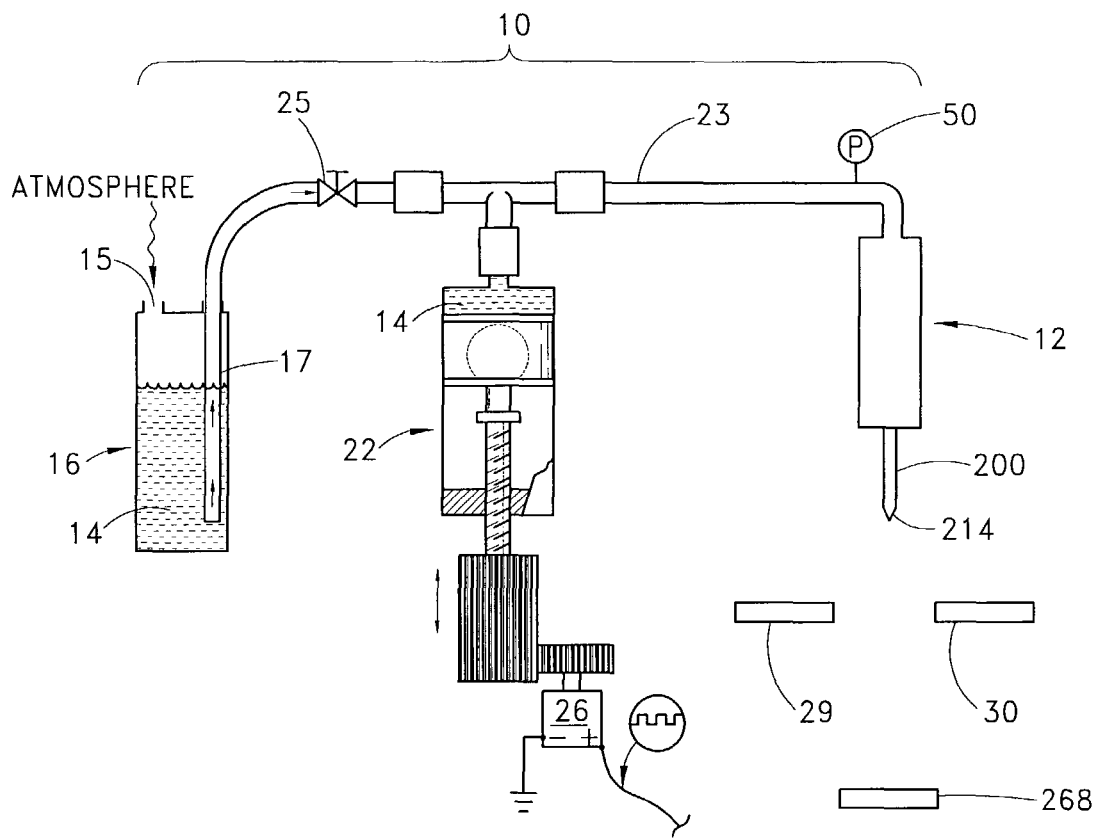
FIG. 7 is a simplified schematic illustration of a microfluidic aspirate-dispense system/apparatus for aspirating and dispensing precise quantities of liquid.
Figure 8:
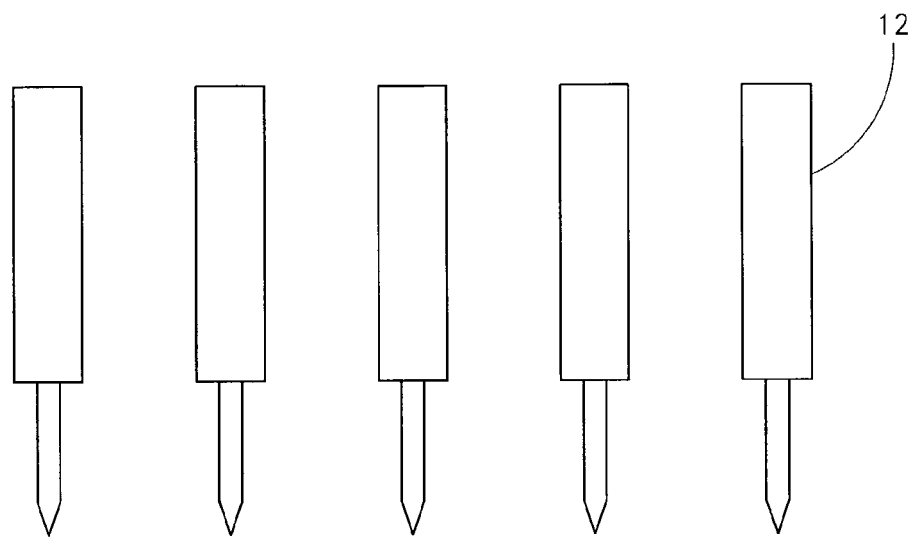
FIG. 8 is a schematic illustration of a one-dimensional array of dispensers.
Figure 9:
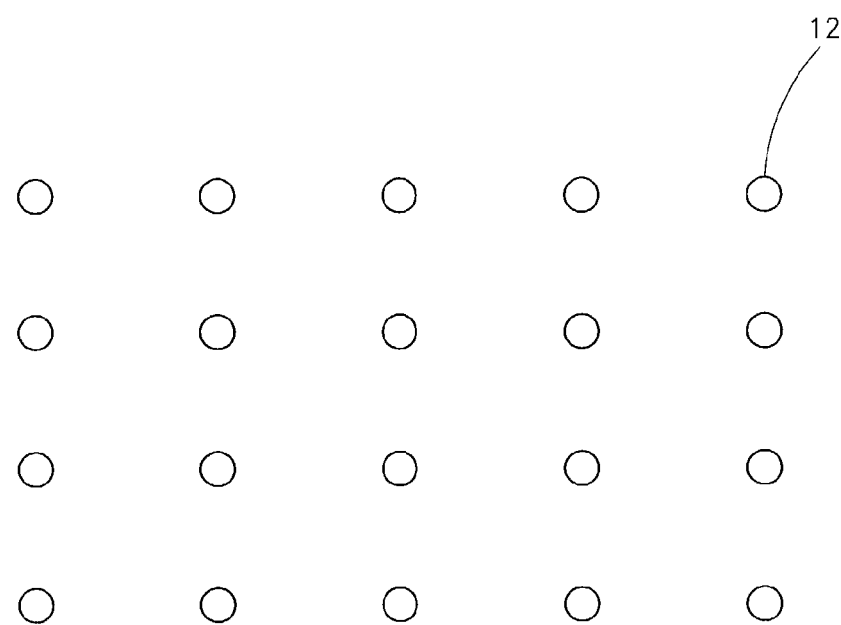
FIG. 9 is a schematic illustration of a two-dimensional array of dispensers.

In one preferred embodiment of the present invention, the tip 200 (FIG. 1) is used for aspirate-dispense operations. FIG. 7 is a schematic drawing of a microfluidic aspirate-dispense apparatus or system 10 having features in accordance with one preferred embodiment. The aspirate-dispense system 10 generally comprises a dispenser 12 with the tip 200 (FIGS. 1 and 7) and a positive displacement syringe pump 22 intermediate a reservoir 16. The dispenser 12 is used to aspirate a predetermined quantity of fluid or reagent from a source or receptacle 29 and dispense a predetermined quantity, in the form of droplets or a spray pattern, of the source fluid onto or into a target 30. The source 29 is typically a microtiter plate, and the target 30 is typically a glass slide, substrate or membrane for genomic microarraying and a microtiter plate for compound reformatting. The positive displacement pump 22 meters the volume and/or flow rate of the reagent aspirated and, more critically, of the reagent dispensed. The reservoir 16 contains a wash or system fluid 14, such as distilled water, which fills most of the aspirate-dispense system 10. One or more robot arms may be used to maneuver the aspirate-dispense system 10 or alternatively the aspirate-dispense system 10 and/or its associated components may be mounted on movable X, X-Y or X-Y-Z platforms. The robot arms and the movable platforms may also be used in combination. In some situations, where large quantities of the same reagent are to be dispensed, the reservoir 16 and syringe pump 22 can be filled with the reagent and the system 10 can be used purely for dispensing. Also, multiple aspirate-dispense systems 10 may be utilized to form a line/one-dimensional array of dispensers 12 (FIG. 8) or a two-dimensional array of dispensers 12 (FIG. 9).

The pump 22 is preferably a high-resolution, positive displacement syringe pump hydraulically coupled to the dispenser 12. Alternatively, pump 22 may be any one of several varieties of commercially available pumping devices for metering precise quantities of liquid. A syringe-type pump 22, as shown in FIG. 7, is preferred because of its convenience and commercial availability. A wide variety of other direct current fluid source means may be used, however, to achieve the benefits and advantages as disclosed herein. These may include, without limitation, rotary pumps, peristaltic pumps, squash-plate pumps, and the like, or an electronically regulated fluid current source.

Figure 10:
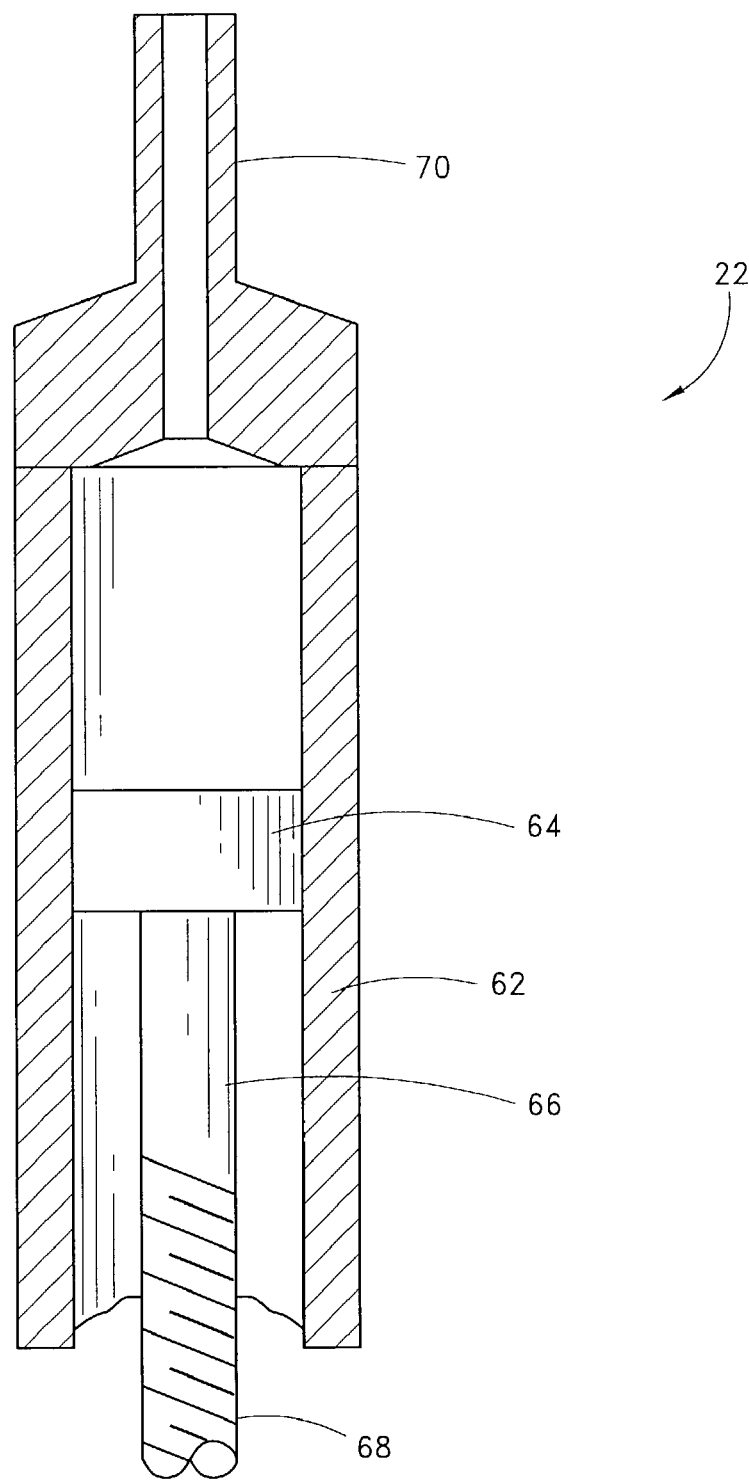
FIG. 10 is a cross-sectional detail view of the syringe pump of FIG. 7.

As illustrated in more detail in FIG. 10, the syringe pump 22 generally comprises a syringe housing 62 of a predetermined volume and a plunger 64 which is sealed against the syringe housing by O-rings or the like. The plunger 64 mechanically engages a plunger shaft 66 having a lead screw portion 68 adapted to thread in and out of a base support (not shown). Those skilled in the art will readily appreciate that as the lead screw portion 68 of the plunger shaft 66 is rotated the plunger 64 will be displaced axially, forcing system fluid from the syringe housing 62 into the exit tube 70. Any number of suitable motors or mechanical actuators may be used to drive the lead screw 68. Preferably, a stepper motor 26 (FIG. 7) or other incremental or continuous actuator device is used so that the amount and/or flow rate of fluid or reagent can be precisely regulated.

Referring to FIG. 7, the syringe pump 22 is connected to the reservoir 16 and the dispenser 12 using tubing 23 provided with luer-type fittings for connection to the syringe and dispenser. Various shut-off valves 25 and check valves (not shown) may also be used, as desired or needed, to direct the flow of fluid 14 to and/or from the reservoir 16, syringe pump 22 and dispenser 12.

Figure 11:
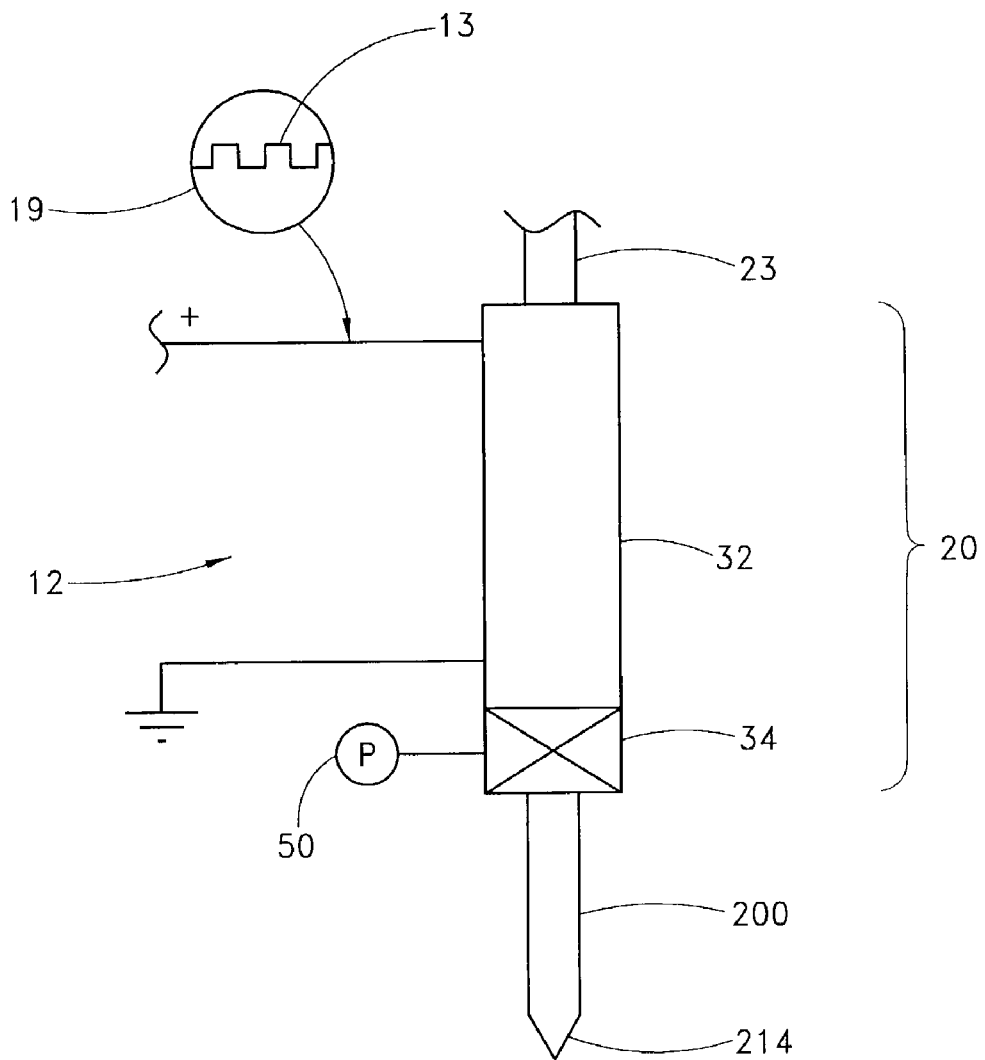
FIG. 11 is a schematic illustration of a solenoid valve dispenser for use in the system of FIG. 7.

In one form of the present invention a solenoid dispenser 12, schematically illustrated in FIG. 11, is preferred. Referring to FIG. 11, the solenoid valve dispenser 12 generally comprises a solenoid-actuated drop-on-demand valve 20, including a valve portion 34 and a solenoid actuator 32, hydraulically coupled to the tube or tip 200 of the present invention. The nozzle 214 of the tip 200 serves as the aspirating and dispensing nozzle. The solenoid valve 20 is energized by one or more electrical pulses 13 provided by a pulse generator 19 to open and close the valve 20 at a predetermined frequency and/or duty cycle. A detailed description of one typical solenoid-actuated valve can be found in U.S. Pat. No. 5,741,554, incorporated herein by reference. The tip (FIGS. 1 and 7) of the present invention may also be used in conjunction with a number of other dispensers well known in the art for dispensing a liquid, such as a piezoelectric dispenser, a fluid impulse dispenser, a heat actuated dispenser or the like.

Referring to FIG. 7, the wash fluid reservoir 16 may be any one of a number of suitable receptacles capable of allowing the wash fluid 14, such as distilled water, to be siphoned into pump 22. The reservoir may be pressurized, as desired, but is preferably vented to the atmosphere, as shown, via a vent opening 15. The particular size and shape of the reservoir 16 is relatively unimportant. A siphon tube 17 extends downward into the reservoir 16 to a desired depth sufficient to allow siphoning of wash fluid 14. Preferably, the siphon tube 17 extends as deep as possible into the reservoir 16 without causing blockage of the lower inlet portion of the tube 17. Optionally, the lower inlet portion of the tube 17 may be cut at an angle or have other features as necessary or desirable to provide consistent and reliable siphoning of wash fluid 14.

Those skilled in the art will recognize that the hydraulic coupling between the pump 22 and the dispenser 12 provides for the situation where the input from the pump 22 exactly equals the output from the dispenser 12 under steady state conditions. Therefore, the positive displacement system uniquely determines the output volume of the system while the operational dynamics of the dispenser 12 serve to transform the output volume into ejected drop(s) having size, frequency and velocity.

It has been discovered, however, that within the aspirate-dispense system 10 there exists an elastic compliance partly due to the compliance in the delivery tubing and other connectors and components, and partly due to gaseous air bubbles that may have precipitated from air or other gases dissolved in the system and/or source fluid. As a result of this elastic compliance, initial efforts to dispense small quantities of fluid resulted in gradually overcoming the system compliance and not in dispensing fluid or reagent. Once this elastic compliance was overcome, a steady state pressure was found to exist and complete dispensing occurred thereafter.

Providing a positive displacement pump 22 in series with a dispenser 12 (FIG. 7) has the benefit of forcing the dispenser 12 to admit and eject a quantity and/or flow rate of reagent as determined solely by the positive displacement pump 22 for steady state operation. In essence, the syringe pump 22 acts as a forcing function for the entire system, ensuring that the desired flow rate is maintained regardless of the duty cycle, frequency or other operating parameters of the dispensing valve, such as the solenoid-actuated valve 20 (FIG. 11). With such configuration and at steady state operation one does not really care what the pressure in the system is because it adjusts automatically to provide the desired flow rate by virtue of having a positive displacement or direct current fluid source as a forcing function for the entire system.

However, this does not address the situation of latent and/or transient pressure variations, such as associated with initial start-up of each dispense and aspirate function. In particular, it has been discovered that the pressure in the system is of critical concern for non-steady state operation involving aspirating or dispensing of microfluidic quantities of reagent or other fluids. Specifically, for an aspirate function it has been discovered that a system pressure close to or below zero is most preferred, while for a dispense function it has been discovered that a finite and positive predetermined steady state pressure is most preferred. The transitions between various modes (aspirate, dispense, purge/wash) and/or flow rates or other operating parameters can result in pressure transients and/or undesirable latent pressure conditions within the aspirate-dispense system 10 (FIG. 7). Purge and wash functions usually entail active dispensing in a non-target position. In some cases, when the same reagent is to be aspirated again, several aspirate-dispense cycles can be performed before executing a purge or wash function. Also, sometimes a purge function may have to be performed during a dispense function, for example, to alleviate clogging due to the precipitation of gaseous bubbles within the system and/or source fluid.

The above discussion highlights the desirability of controlling the hydraulic pressure within a microfluidic aspirate-dispense system. In one preferred embodiment, a pressure pre-conditioning method causes a steady state pressure to exist within a liquid delivery system, such as the positive-displacement aspirate-dispense system 10 (FIG. 7), prior to initiating dispensing operations. The initial positive pressure overcomes the system's elastic compliance and thereby achieves a steady state pressure condition prior to dispensing. Advantageously, this assures that the fluid displaced by the syringe pump 22 (FIG. 7) will be completely transferred as output to the system nozzle, such as the nozzle 214 (FIGS. 1 and 7).

One preferred pressure pre-conditioning method facilitates the aspirate-dispense process by providing an efficient pressure compensation scheme which is efficient in both fluid or reagent consumption and time. To illustrate this method, reference will be made to the aspirate-dispense system 10, the syringe pump 22 and the solenoid-actuated dispenser 12, though other liquid delivery systems, direct current fluid sources and dispensers may be utilized with efficacy, as required or desired, giving due consideration to the goal of providing an efficient pressure compensation scheme for aspirate and/or dispense functions.

Figure 12:
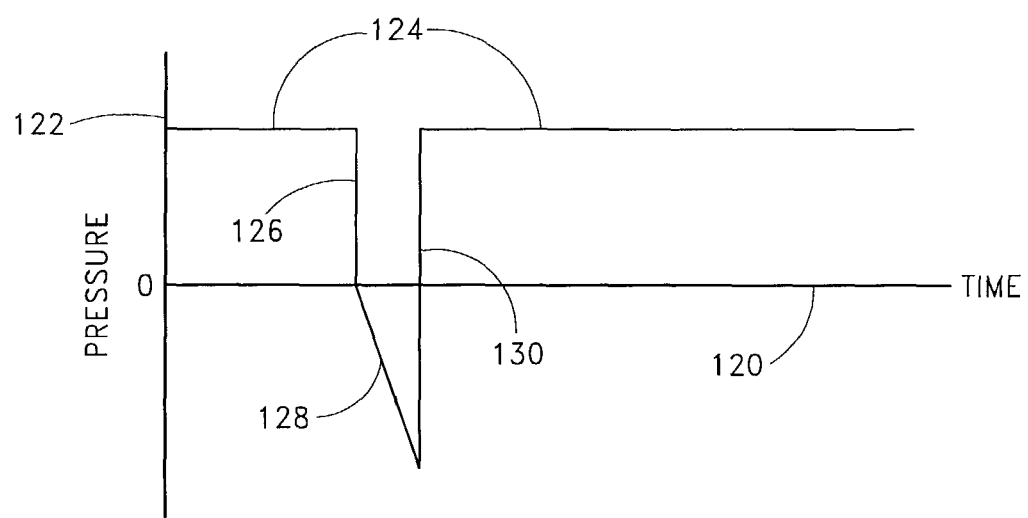
FIG. 12 is a schematic graph (not to scale) of system pressure versus time illustrating a pressure pre-conditioned aspirate-dispense cycle.

FIG. 12 shows a schematic graph (not to scale) illustrating the pressure-time history for a pressure compensated aspirate-dispense cycle in accordance with one preferred pressure pre-conditioning/compensation method of the invention. The x-axis 120 represents the time and the y-axis 122 represents the system pressure. Line 124 depicts the predetermined and/or steady state pressure during which dispensing occurs, line 126 depicts the pressure compensation prior to the aspirate function, line 128 depicts the pressure during the aspirate function, and line 130 depicts the pressure compensation prior to the dispense function.

As indicated before, just preceding an aspirate function a system pressure close to or below zero is preferred. Referring to FIG. 12, this is achieved by first "venting" the system (line 126) to release the pressure. This may be done in a variety of ways, such as performing a series of rapid waste dispenses. For example, the nozzle 214 (FIGS. 1 and 7) may be positioned over a waste receptacle (not shown) and the drop-on-demand valve 20 (FIG. 11) opened and closed rapidly without operating the syringe pump 22 (FIG. 7). The opening of the valve 20 causes some system fluid 14 (FIG. 7) and/or any residual aspirated source fluid from the prior aspirate function to be dispensed into the waste position due to the dispense steady state pressure (line 124) or any residual pressure within the system 10 (FIG. 7). After several valve openings the residual pressure (line 124) dissipates and the system pressure stabilizes to a value near zero. Desirably, this "venting" of system pressure can concurrently serve as a wash function.

Alternatively, the valve 20 (FIG. 11) may remain closed while the syringe pump 22 (FIG. 7) is operated in the reverse direction, as required to release system pressure. The residual pressure may also be released by providing a separate relief valve (not shown) for the syringe pump 22 (FIG. 7) or the shut-off valve 25 (FIG. 7) can be opened to release system fluid 14 (FIG. 7) back into the reservoir 16 (FIG. 7).

Advantageously, and referring to FIG. 12, at this point the source fluid from the source 29 (FIG. 7) can be aspirated (line 128) without the spurious dispense or ejection of system fluid 14 (FIG. 7) and/or residual aspirated fluid into the source 29 (FIG. 7). The nozzle 214 (FIGS. 7 and 11) is placed or dipped in the source 29 and, with the valve 20 (FIG. 11) open, the syringe pump 22 (FIG. 7) is operated in the reverse direction, creating a reduced or negative pressure (line 128), to aspirate source fluid or reagent into the tip 200 (FIG. 7) of the aspirate-dispense system 10 (FIG. 7). Preferably, the valve 20 (FIG. 11) is open continuously during aspiration, that is, a 100% duty cycle is utilized. Advantageously, since the system pressure is at or close to zero, predetermined small volumes of source fluid can be substantially accurately aspirated by metering the displacement of the syringe pump 22 (FIG. 7). Also, by preferably utilizing an optimally slow motion of the syringe pump plunger 64 (FIG. 10) while having the valve 20 (FIG. 11) fully open, the reduced/negative aspirate system pressure is kept close to zero so that the flow of source fluid into the tip 200 and nozzle 214 (FIG. 7) is maintained generally laminar. The displacement rate of the syringe pump plunger 64 (FIG. 10) is dependent on the volume to be aspirated, but it is typically in the range of about 0.5 to 50 µL/sec. For aspiration of very small volumes the plunger displacement rate is about 0.5 µL/sec. Moreover, utilizing a 100% valve duty cycle, during aspiration, further assists in maintaining a generally laminar flow of source fluid into the nozzle 214 and tip 200. Thus, turbulent mixing of source fluid with system fluid 14 (FIG. 7) is reduced, and any dilution of the source fluid will essentially be due to diffusion. Advantageously, in most cases, at or near room temperature, the diffusion process is very slow, and hence the overall effective dilution of the source fluid or reagent is small or negligible.

The aspiration process (line 128 in FIG. 12) results in a partial vacuum or residual reduced/negative pressure within the aspirate-dispense 10 (FIG. 7), which is less than the preferred dispense steady state pressure (line 124). For effective and accurate dispensing of aspirated fluid the system pressure is preferably raised from the reduced or negative value to a positive dispense steady state and/or predetermined value. A simple, fast technique to raise the system pressure to the preferred dispense pressure is by displacing the syringe pump plunger 64 (FIG. 10) in the forward direction while keeping the drop-on-demand valve 20 (FIG. 11) in the closed position. This preferred "pressurizing" pressure compensation is illustrated by line 130 (FIG. 12).

Once the system pressure has been raised to the nominal steady state dispense pressure (line 124), the predetermined quantity or quantities of aspirated source fluid can be accurately dispensed. During dispensing the displacement of the syringe pump plunger 64 (FIG. 10) can be synchronized with the duty cycle of the drop-on-demand valve 20 (FIG. 11) or, alternatively, the pump 22 (FIG. 7) can be used to supply a generally continuous flow rate. Advantageously, such a pressurization scheme is efficient, does not waste reagent and reduces reagent dilution.

In one embodiment, the above pressurization scheme can also be followed by a pre-dispense operation for fine tuning of the system pressure to the desired steady state and/or predetermined value. This pre-dispense typically involves dispensing a small quantity of fluid back into the aspiration fluid source. The pre-dispense may also be performed by dispensing in a waste position. Advantageously, after the pressurization scheme the system pressure is sufficiently close to the steady-state and/or predetermined value, and hence this pre-dispensing of fluid results in small, negligible or no wastage of fluid.

In general, the pressure compensation methods discussed herein may be employed whenever transient pressure variations occur in the aspirate and/or dispense hydraulic system, giving due consideration to achieving the goal of providing predetermined and/or steady state pressures. These pressure transients may occur due to hydraulic "capacitance effect", leakage or the precipitation of small gaseous bubbles, or during initial start-up or intermittent dispensing operations.

The importance of performing aspirate and dispense functions at the optimal pressures has been illuminated so far. The amount of pre-pressurization needed to achieve steady state operation may be determined empirically for a given set-up. An experimental parametric analysis may be performed for a given set-up and several correlations can be obtained. This open-loop control technique will assist in determining the actuations of the syringe pump 22 (FIG. 7) to achieve the optimal operating pressure.

Another preferred approach of estimating the steady state pressure dispense pressure and the system elastic compliance utilizes a semi-empirical methodology. In this case, one or more pressure sensors 50 (FIGS. 7 and 11) may be included to monitor the system pressure. The pressure measurements as provided by one or more pressure sensors 50 (FIGS. 7 and 11) can also be used to provide diagnostic information about various fluid and flow parameters of the hydraulic system. The pressure sensors 50 can be placed at the drop-on-demand valve 20 (FIG. 11) and/or at appropriate positions intermediate the syringe pump 22 (FIG. 7) and the dispenser 12 (FIG. 7), such as on the feedline 23, as illustrated in FIG. 7. Of course, the pressure sensors 50 may also be placed at other suitable locations, as required or desired, giving due consideration to the goals of providing pressure compensation and reliable aspiration and dispensing. Suitable pressure sensors 50 are well known by those of ordinary skill in the art and, accordingly, are not described in greater detail herein. The semi-empirical approach utilizes fluid flow theory and measurements from one or more pressure sensors 50 positioned at suitable locations.

The apparatus or system 10 (FIG. 7) may be used for a wide variety of microfluidic applications such as printing of microarrays and high throughput screening, among others. The operation of the aspirate-dispense system 10 (FIG. 1) may be monitored and controlled by a suitable automated control system. Additionally, the control system may be interfaced with any robot arms and/or X, X-Y or X-Y-Z movable platforms used in conjunction with the aspirate-dispense system 10, source 29, target 30 and waste receptacle to facilitate maneuverability of the various components of the system and its associated elements.

The system 10 (FIG. 7) can also be used for contact deposition of source fluid onto the target 30. By adjusting the open time of the valve 20 (FIG. 11) and selecting the appropriate dimensions for the nozzle 214 (FIGS. 1 and 7) a drop can be formed at the nozzle end 205 by incrementing the syringe pump 22 (FIG. 7). The drop can then be applied to the target 30. Multiple touch-offs can also be performed, as required or desired.

In one embodiment, the system 10 can also be operated without the dispenser 12. The syringe pump 22 is operated in the reverse direction to aspirate fluid. The source fluid can then be transferred to the target 30 by non-contact dispensing or contact deposition.

The tip 200 (FIGS. 1 and 7) provides several benefits and advantages in conjunction with the aspirate-dispense system 10 (FIG. 7). The tip outer taper 204 and the small outer diameter at the nozzle end 205 leads to less accumulation of fluid on the outer surface of the tip 200 and this improves the reliability, repeatability and accuracy of the system 10. In one embodiment, a wash station 268 (FIG. 7) with a vacuum dry system 79 (FIGS. 6A-6B) is provided with the system 10 (FIG. 7) to maintain a dry tip. The vacuum dry system 79 is used to remove any remove any excess fluid that may have adhered to the outer surface of the tip 200 (FIGS. 1 and 7) during aspiration, wash/purge steps or due to any moisture build-up on the outer surface of the tip 200, for example, due to condensation from the air environment, as discussed above for the random access print head 230 (FIG. 3). This further improves the repeatability and accuracy of the system 10.

The vacuum dry can also be performed after washing the tip 200 (FIGS. 1 and 7) in a cleaning fluid, for example, distilled water, among others. Alternatively, the tip 200 can be dipped in a volatile solvent such as isopropyl alcohol, among others, to maintain a dry tip. Also, as indicated above, the hydrophobic coating 220 (FIG. 2) and the outer taper 204 (FIG. 1) to a small nozzle end 205 (FIG. 1) further assist in keeping the tip 200 dry and free of excess liquid. This further improves the repeatability and accuracy of the aspirate-dispense system 10 (FIG. 7).

The inner taper 212 (FIG. 1) of the tip 200 (FIGS. 1 and 7) also improves the performance of the system 10 (FIG. 7) in terms of less precipitation of gaseous bubbles within the source reagent and/or the system fluid 14. This is because the inner taper 212 results in smaller local pressure drops during dispensing and aspiration. The inner taper 212 also reduces the mixing of source reagent with the system fluid 14 by further improving the generally laminar flow during aspiration. Advantageously, this reduces the wastage of valuable reagent.

Figure 13:
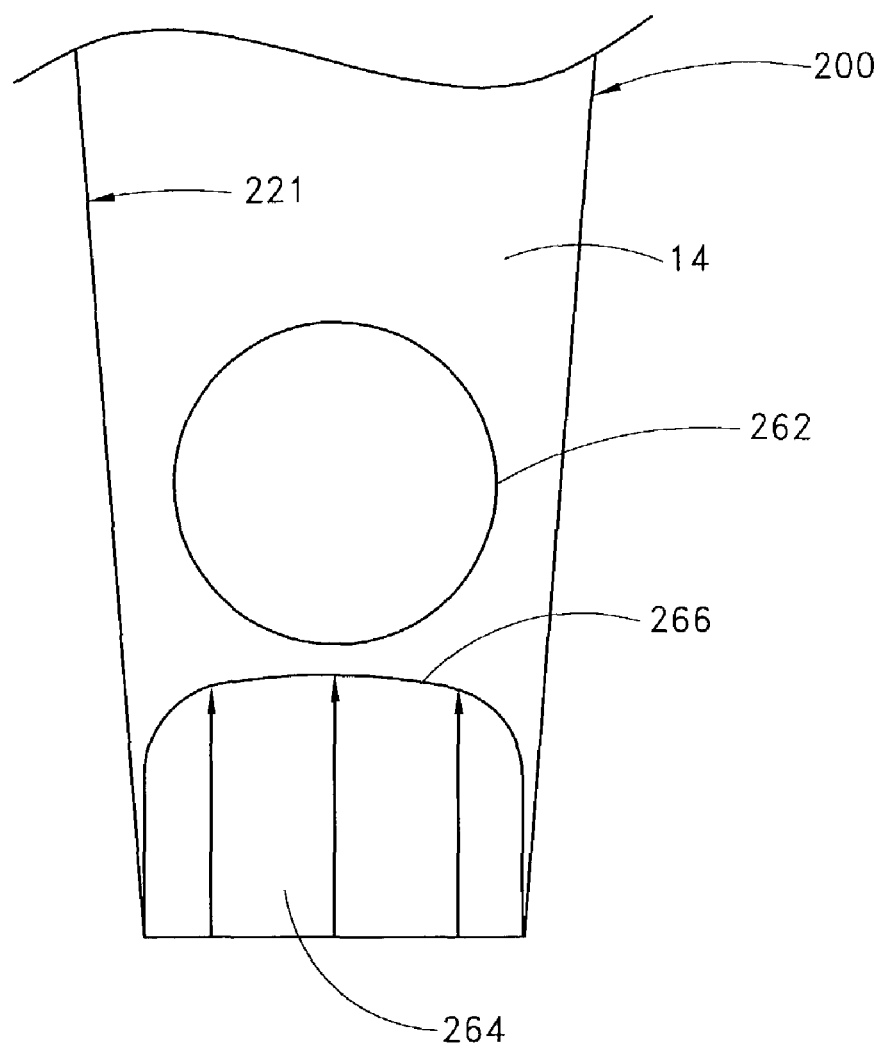
FIG. 13 is a schematic illustration of an aspirate function in accordance with one preferred embodiment of the present invention.

In one preferred embodiment, prior to aspiration of source fluid the syringe pump 22 (FIG. 7) is operated in the reverse direction with the nozzle orifice 216 (FIG. 1) exposed to the atmosphere to draw a small quantity of air into the tip 200. Referring to FIG. 13, this forms a small air bubble 262 within the system fluid 14 in the tip 200. The volume of the bubble 262 can be in the range from less than about 0.5 μL to greater than about 1.0 μL. The tip 200 is then dipped in the source fluid and the syringe pump 22 is decremented to aspirate source fluid 264 (FIG. 13) into the tip 200. In effect, the bubble 262 causes the aspirated fluid laminar velocity profile 266 to have a generally blunt shape by reducing the fluid drag imposed on the aspirated fluid 264 near the tip inner surface or wall 221. Advantageously, this reduces the area of the interface between the system fluid 14 and the aspirated source fluid 264, and hence desirably reduces the mixing and dilution of the aspirated fluid 264 with the system fluid 14.

As indicated above, for DNA microarraying the target 30 is generally a glass slide, substrate or membrane, among others, and the system 10 (FIG. 7) is used to form dots or spots of the source fluids on the target 30. For DNA microarraying the system 10 can form dots having a diameter in the range from about 50 μm to greater than about 400 μm and can form arrays having densities in the range from less than about 10 dots/cm$^2$ to greater than about 6000 dots/cm$^2$. For touch-off deposition the size of these spots or dots is generally determined by the outer diameter of the nozzle end 205 of the tip 200. The system 10 can also transfer fluid volumes as low as in the picoliter range and up to about 100 nanoliter (nL) or more.

For high throughput screening (compound reformatting) the target 30 is typically a microtiter plate, such as a 96, 384 or 1536 well plate. In this case, the system 10 can transfer fluid volumes in the range from about 1 nL to about 200 nL or more.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. An apparatus for aspirating and dispensing predetermined microfluidic quantities of a fluid, comprising:
   a ceramic tip including a nozzle with an inner taper to provide improved and generally laminar flow, at least a portion of said tip comprising a hydrophobic coating;
   a drop-on-demand valve adapted to be opened and closed at a predetermined frequency and/or duty cycle to permit intermittent hydraulic coupling with said tip; and
   a positive displacement pump hydraulically coupled with said valve for metering predetermined quantities of fluid to or from said tip.

2. A method for using the apparatus of claim 1 to dispense a fluid from a fluid source onto a desired target substrate, comprising the following steps:
   operating said pump in a reverse direction to draw a small quantity of air into said tip and thereby form an air bubble within system fluid present in said tip;
   dipping said nozzle in said fluid source;
   operating said pump in the reverse direction to create a reduced pressure to thereby allow a quantity of fluid from said fluid source to be aspirated into said tip; and
   operating said pump in a forward direction to dispense a predetermined quantity of fluid onto said target substrate.

3. The apparatus of claim 1, wherein said tip comprises a lumen that extends substantially completely through said tip to form an orifice at a lower-most end of said nozzle.

4. The apparatus of claim 3, wherein said lumen comprises a substantially cylindrical upper portion and a substantially tapered lower portion.

5. The apparatus of claim 4, wherein said upper and lower portions are coaxially aligned relative to one another about a central axis and said lower-most end is substantially flat and lies in a plane substantially normal to said ventral axis.

6. The apparatus of claim 5, wherein said nozzle comprises at least a portion of said tapered lower portion adjacent said orifice and has an inner diameter adjacent said orifice.

7. The apparatus of claim 6, wherein said upper portion has a first inner diameter and said lower portion has a second inner diameter and wherein said second inner diameter is smaller than said first inner diameter.

8. The apparatus of claim 6, wherein the inner diameter of said nozzle adjacent said orifice is about 20 microns (μm) to about 180 microns (μm).

9. The apparatus of claim 7, wherein said tip comprises a substantially cylindrical upper body portion having a first outside diameter and a substantially tapered lower body portion having a second outside diameter at a transition portion thereof which is substantially equal to said first outside diameter of said upper body portion and a third outer diameter at said lower-most end thereof which is smaller than said first or second outside diameters.

10. The apparatus of claim 9, wherein said upper and lower body portions are coaxially aligned relative to one another about said central axis.

11. The apparatus of claim 9, wherein said ceramic tip comprises alumina.

12. The apparatus of claim 9, wherein at least said lower body portion is coated on the outside with a hydrophobic coating.

13. The apparatus of claim 9, wherein at least said lower body portion is coated on the outside with a film or coating of material selected from the group: silicon nitride, silicon carbide or titanium nitride.

14. The apparatus of claim 1, wherein said apparatus further comprises a vacuum dry system including at least one vacuum cavity to facilitate in cleaning said tip.

15. The apparatus of claim 14, wherein said vacuum cavity comprises at least one seal and/or step that engages at least one outer surface of said tip to facilitate removal or clearing of fluid from inside said tip.

16. The apparatus of claim 14, wherein said vacuum dry system further comprises a pump to remove excess fluid from an outer surface of said tip.

17. The apparatus of claim 16, wherein said pump is configured such that it removes excess fluid from said outer surface of said tip without disturbing fluid present inside said tip.

18. The apparatus of claim 5, wherein said lower-most end of said nozzle has an outer diameter greater than the effective diameter of a drop dispensed by said apparatus.

19. The apparatus of claim 18, wherein said apparatus is operable to dispense a drop having a volume less than about 100 nanoliters (nL).

20. The apparatus of claim 18, wherein said outer diameter of said lower-most end is about 400 microns (μm) to about 900 microns (μm).

21. The apparatus of claim 20, wherein said apparatus is operable to dispense a drop having a volume less than about 100 nanoliters (nL).

22. The apparatus of claim 21, wherein said drop has a volume of about 10 nanoliters (nL).

23. The apparatus of claim 21, wherein said drop has a volume of about 1 nanoliter (nL).

24. A method for using the apparatus of claim 1 to dispense a first fluid from a source onto or into a target, comprising:
   operating said pump to draw a quantity of a second fluid into said tip such that said second fluid does not substantially mix with system fluid present in said tip and forms a discrete volume in said tip;
   dipping said nozzle in said source;
   operating said pump to aspirate a quantity of said first fluid from said source into said tip;
   whereby, presence of said second fluid in said tip allows the flow profile during aspiration of said first fluid to be substantially laminar and mitigates or substantially prevents mixing and dilution of said aspirated first fluid with said system fluid.

25. The method of claim 24, wherein said method further comprises operating said pump to dispense a quantity of said first fluid onto or into said target.

26. The method of claim 24, wherein said second fluid comprises a gas.

27. The method of claim 26, wherein said gas comprises air and forms an air bubble within said tip.

* * * * *

UNITED STATES PATENT AND TRADEMARK OFFICE
CERTIFICATE OF CORRECTION

PATENT NO. : 7,736,591 B2  
APPLICATION NO. : 10/421636  
DATED : June 15, 2010  
INVENTOR(S) : Don Rose et al.

Page 1 of 1

It is certified that error appears in the above-identified patent and that said Letters Patent is hereby corrected as shown below:

Title Page, in Item (56), page 1, column 2, line 6, under Other Publications, please change "Mlcroarray" to --Microarray--.

Title Page, in Item (56), page 1, column 2, line 8, under Other Publications, change "839" to --639--.

Title Page, in Item (56), page 2, column 2, line 34, under Other Publications, change "Jacob," to --Jacobs,--.

Title Page, in Item (56), page 2, column 2, line 40, under Other Publications, change "Mlcroarray" to --Microarray--.

At column 17, line 43, in Claim 5, change "ventral" to --central--.

Signed and Sealed this  
Fourth Day of January, 2011

David J. Kappos  
*Director of the United States Patent and Trademark Office*